(12) United States Patent
Fisker et al.

(10) Patent No.: US 10,706,184 B2
(45) Date of Patent: *Jul. 7, 2020

(54) DESIGNING A VIRTUAL PREPARATION AND A VIRTUAL GINGIVAL

(71) Applicant: 3Shape A/S, Copenhagen K (DK)

(72) Inventors: Rune Fisker, Virum (DK); Sven Nonboe, Hillerød (DK)

(73) Assignee: 3Shape A/S, Copenhagen K (DK)

( * ) Notice: Subject to any disclaimer, the term of this patent is extended or adjusted under 35 U.S.C. 154(b) by 372 days.

This patent is subject to a terminal disclaimer.

(21) Appl. No.: 15/705,898

(22) Filed: Sep. 15, 2017

(65) Prior Publication Data

US 2018/0081996 A1 Mar. 22, 2018

Related U.S. Application Data

(63) Continuation of application No. 13/881,515, filed as application No. PCT/DK2011/050409 on Oct. 31, 2011, now Pat. No. 9,767,223.

(30) Foreign Application Priority Data

Oct. 29, 2010 (DK) .................................. 2010 00982
Feb. 10, 2011 (DK) .................................. 2011 00088
Oct. 4, 2011 (DK) .................................. 2011 00758

(51) Int. Cl.
*G06F 17/50* (2006.01)
*G06F 30/00* (2020.01)
(Continued)

(52) U.S. Cl.
CPC .............. *G06F 30/00* (2020.01); *B33Y 50/00* (2014.12); *B33Y 80/00* (2014.12); *G16H 20/40* (2018.01)

(58) Field of Classification Search
CPC .......... G06F 17/50; B33Y 50/00; B33Y 80/00; G16H 20/40; A61C 13/0004
(Continued)

(56) References Cited

U.S. PATENT DOCUMENTS 5,738,678 A 4/1998 Patel
9,767,223 B2 * 9/2017 Fisker .................... B33Y 50/00
(Continued)

FOREIGN PATENT DOCUMENTS

WO 2005077296 8/2005
WO WO 2006/092800 A2 9/2006
(Continued)

OTHER PUBLICATIONS

International Search Report (PCT/ISA/210) dated Dec. 1, 2011, by the Danish Patent Office as the International Searching Authority for International Application No. PCT/DK2011/050409.
(Continued)

*Primary Examiner* — Dwin M Craig
(74) *Attorney, Agent, or Firm* — Buchanan Ingersoll & Rooney PC

(57) ABSTRACT

A computer product for generating a digital 3D model for use in a dental component based on a digital 3D model of the dental component showing a shape of the teeth and a digital 3D representation of a pre-prepared set of teeth showing the region for which the dental component is intended, said product causing a system to generate a digital 3D combined model representing a target dental situation when the dental component is arranged at the teeth, where the instructions are configured for digitally replacing one or more teeth of the digital 3D representation of the pre-prepared set of teeth with the digital 3D model of the dental component by digitally removing the one or more teeth of the digital 3D representation of the pre-prepared set of teeth and adding the
(Continued)

digital 3D model of the dental component to the digital 3D representation of the pre-prepared set of teeth.

15 Claims, 31 Drawing Sheets

(51) Int. Cl.
*B33Y 80/00* (2015.01)
*B33Y 50/00* (2015.01)
*G16H 20/40* (2018.01)

(58) Field of Classification Search
USPC .............................................................. 703/1
See application file for complete search history.

(56) References Cited

U.S. PATENT DOCUMENTS

| | | |
|---|---|---|
| 2003/0096210 A1 | 5/2003 | Rubbert et al. |
| 2004/0029068 A1 | 2/2004 | Sachdeva et al. |
| 2004/0081938 A1 | 4/2004 | Chishti et al. |
| 2005/0089822 A1 | 4/2005 | Geng |
| 2006/0105294 A1 | 5/2006 | Burger et al. |
| 2009/0246726 A1 | 10/2009 | Chelnokov et al. |
| 2009/0248184 A1 | 10/2009 | Steingart et al. |
| 2009/0319068 A1 | 12/2009 | Sager |

FOREIGN PATENT DOCUMENTS

| | | |
|---|---|---|
| WO | WO 2009/094576 A1 | 7/2009 |
| WO | WO 2009/146164 A1 | 12/2009 |
| WO | WO 2010/105628 A2 | 9/2010 |

OTHER PUBLICATIONS

First Office Action and Danish Search Report dated May 26, 2011, issued by Danish Patent Office in corresponding Danish Patent Application No. PA 2010 00982. (1 page).

First Office Action and Danish Search Report dated Sep. 19, 2011, issued by Danish Patent Office in corresponding Danish Patent Application No. PA 2011 00088. (1 page).

Extended European Search Report issued in corresponding European Patent Application No. 19 16 6947, dated Sep. 30, 2019 (8 pages).

* cited by examiner

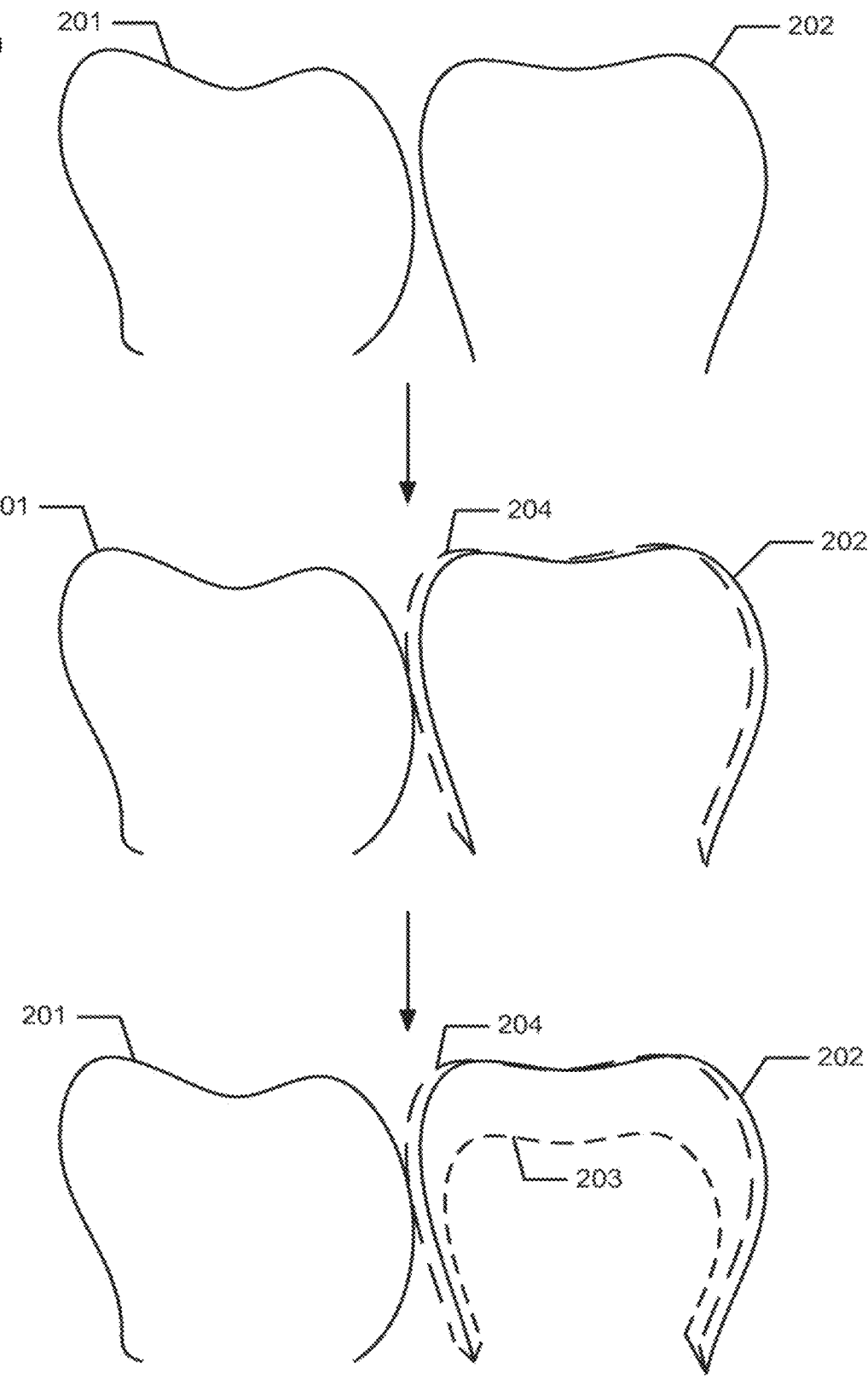

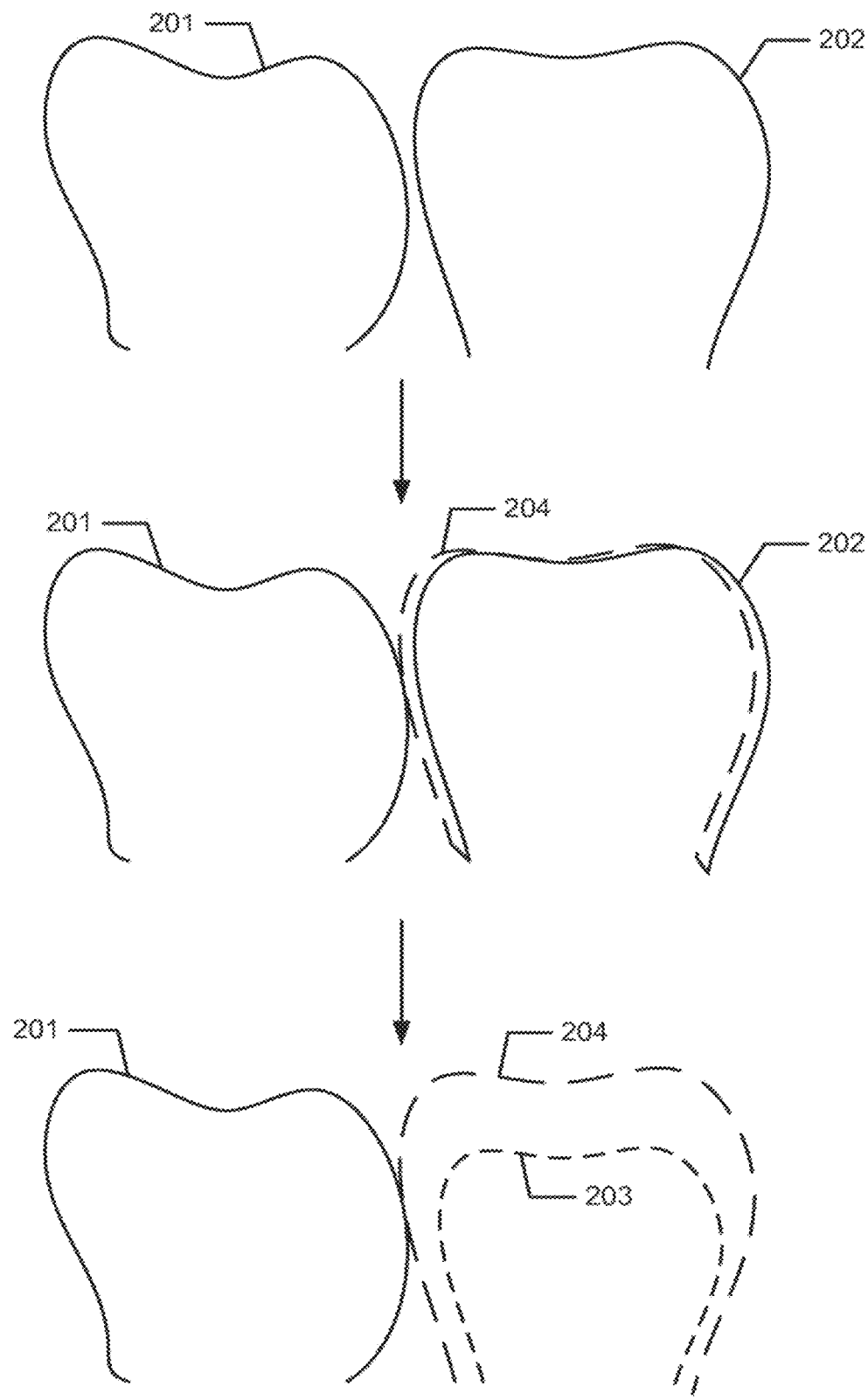

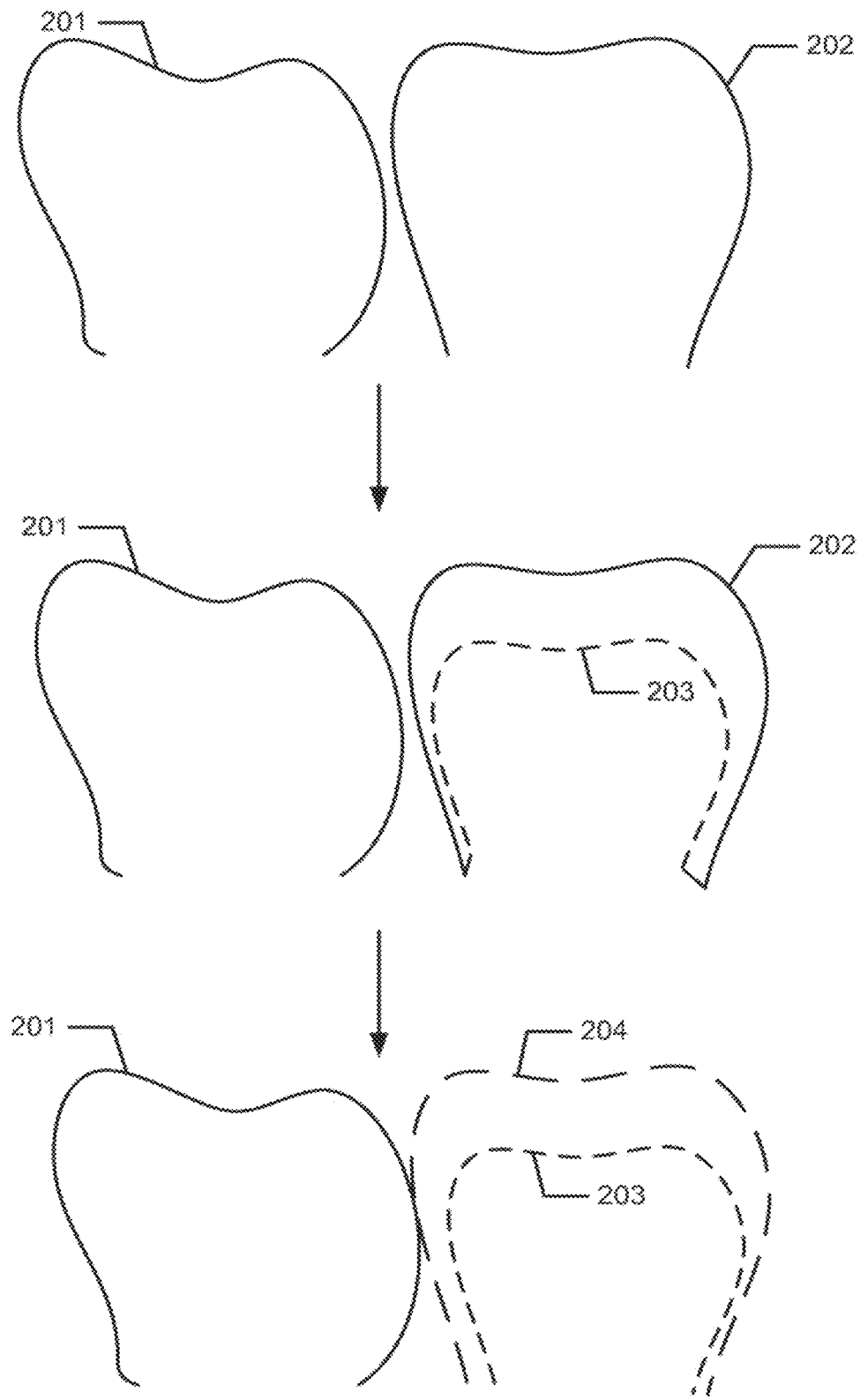

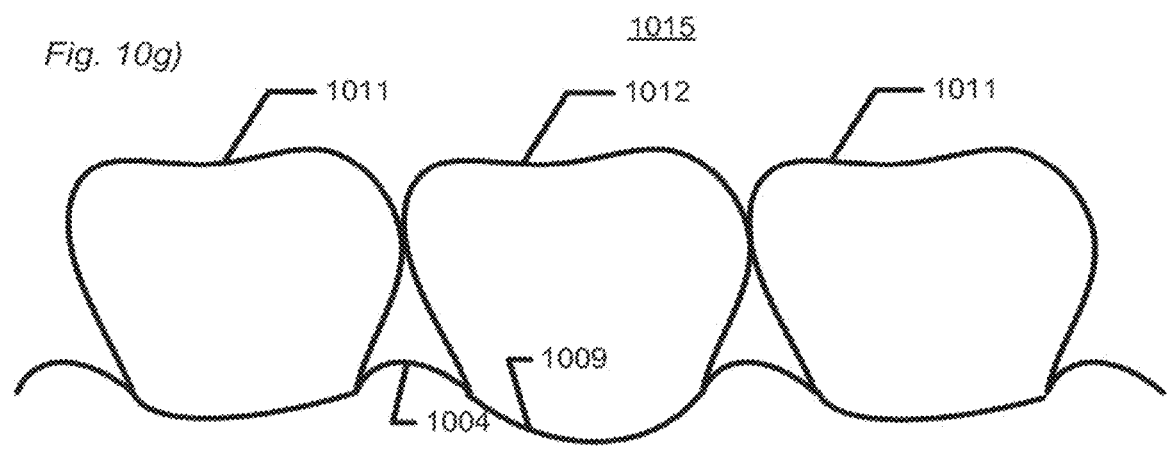
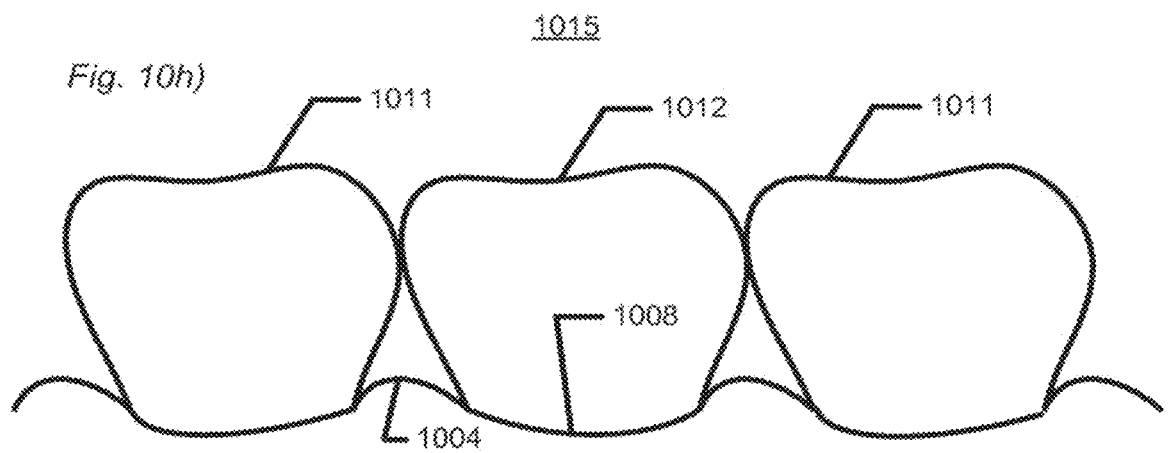

PRIOR ART

DESIGNING A VIRTUAL PREPARATION AND A VIRTUAL GINGIVAL

CROSS REFERENCE TO RELATED APPLICATIONS

The present application is a continuation of U.S. patent application Ser. No. 13/881,515, which was filed in the U.S. on Apr. 25, 2013, now U.S. Pat. No. 9,767,223, and which is a national stage of PCT International Application No. PCT/DK2011/050409, filed Oct. 31, 2011, which claims priority of Danish Patent Application No. PA 2011 00758, filed Oct. 4, 2011, which claims the benefit of U.S. Provisional Patent Application No. 61/542,682, filed Oct. 3, 2011, which claims priority of Danish Patent Application No. PA 2011 00088, filed Feb. 10, 2011, which claims the benefit of U.S. Provisional Patent Application No. 61/441,373, filed Feb. 10, 2011 which claims priority of Danish Patent Application No. PA 2010 00982, filed Oct. 29, 2010, and which claims the benefit of U.S. Provisional Patent Application No. 61/408,026, filed Oct. 29, 2010. The subject matter of U.S. patent application Ser. No. 13/881,515; PCT International Application No. PCT/DK2011/050409; Danish Patent Application No. PA 2011 00758; U.S. Provisional Patent Application No. 61/542,682; Danish Patent Application No. PA 2011 00088; U.S. Provisional Patent Application No. 61/441,373, Danish Patent Application No. PA 2010 00982, and U.S. Provisional Patent Application No. 61/408,026 are incorporated herein by reference.

FIELD OF THE INVENTION

This invention generally relates to a system and a method which can be used in relation to designing a dental component for a region on a patient's set of teeth. More particularly, the invention relates to obtaining a digital 3D representation of at least the region of the patient's set of teeth, where the digital 3D representation is based on a 3D scan.

BACKGROUND OF THE INVENTION

WO10105628 discloses a method for planning, visualizing, and/or optimizing dental restoration on at least a part of the pre-prepared teeth of a patient, wherein said method comprises the steps of:
  providing at least one 3D digital model of at least a part of the pre-prepared teeth;
  designing at least one dental restoration CAD model based on the 3D digital model of at least a part of the pre-prepared teeth;
  providing at least one 3D digital model of at least a part of the prepared teeth, where the prepared teeth are provided by preparing the pre-prepared teeth by dental restorative work, at least partly based on the dental restoration CAD model; and
  aligning the 3D models of the pre-prepared and the prepared teeth.

WO09146164A discloses a method of creating a 3-D anatomic digital model for determining a desired location for placing at least one dental implant in a patient's mouth. The method comprises the act of obtaining a first dataset associated with hard tissue of the patient's mouth. The method further comprises the act of obtaining a second dataset associated with soft tissue of the patient's mouth. The method further comprises the act of combining the first dataset and the second dataset to create a detailed structure of hard tissue and soft tissue having variable dimensions over the hard tissue.

US2004081938A discloses that a computer obtains a digital model of a patient's dentition, including a dental model representing the patient's teeth at a set of initial positions and a gingival model representing gum tissue surrounding the teeth. The computer then derives from the digital model an expected deformation of the gum tissue as the teeth move from the initial positions to another set of positions.

It remains a problem to provide improved planning and virtual designing of a dental component, such as a restoration, a temporary restoration or a diagnostic wax-up, for a patient.

SUMMARY

Disclosed is a method for generating a 3D virtual model of a dental component for a region of a patient's set of teeth, where the dental component comprises a temporary bridge restoration or a diagnostic wax-up bridge, such that the dental component comprises crowns and at least one pontic, wherein the method comprises:
  obtaining a digital 3D representation of the set of teeth, where the digital 3D representation is based on a 3D scan of a pre-prepared configuration of the set of teeth;
  virtually sectioning the part of the digital 3D representation corresponding to the teeth in said region using at least one 3D sectioning spline;
  determining at least part of the inter-proximal surfaces of the virtually sectioned teeth; and
  determining a jaw-facing surface for the dental component, where the jaw-facing surface is configured for facing a surface which is not available in the digital 3D representation of the pre-prepared set of teeth.

When discussing a relation between a feature of the dental component and a part of the patient's set of teeth, such as pre-prepared or prepared teeth or the gingival, it is contemplated that the dental component is arranged in relation to the patient's set of teeth. This may be the case for the virtual 3D model of the dental component and a digital 3D representation of the set of teeth, as well as for the manufactured dental model and the patient's set of teeth.

In the context of the present invention, the phrase "the surface which is not available in the 3D representation of the pre-prepared set of teeth" may be the surface of a tooth after its preparation for accepting a crown, such as a crown of a bridge restoration, or the surface of the gingival after a tooth has been extracted to make place for the pontic part of a bridge restoration. In relation to the gingival, the surface may be as it is just after the removal of a tooth, or some time thereafter such that the gingival has had time to heal.

The virtually sectioning the part of the digital 3D representation corresponding to the teeth in said region using at least one 3D sectioning spline may comprise using a separate 3D sectioning spline for each tooth which is sectioned, or using a 3D sectioning spline which is for sectioning two or more teeth. The 3D sectioning spline may enclose a group of teeth, such that the 3D sectioning spline extends over the most distant inter-proximal surfaces in the group of teeth.

The region of a patient's set of teeth may comprise teeth which are to be extracted and replaced by a pontic, and teeth that are to be prepared for accepting a crown portion of e.g. a temporary bridge restoration.

Similar to a permanent bridge restoration a temporary bridge restoration and a diagnostic wax-up bridge may comprise at least one pontic and crowns for anchoring the dental component in the patient's mouth, such as for anchoring the dental component on teeth that are prepared for accepting a crown. The pontic may provide a dental restoration for a broken or dead tooth, while the neighboring teeth are to be prepared for accepting the crowns of the bridge.

In the context of the present invention, the phrase "jaw-facing surface" may refer to a surface of a dental component facing the jaw at which the dental component is configured to be arranged at.

The jaw-facing surface of the dental component may also be referred to as the edge of the dental component, such that e.g. the phrase "the pontic edge" can be used in relation to the jaw-facing surface of the pontic.

In the case of a pontic of a dental bridge, the jaw-facing surface of the dental component may be the surface facing the gingival. The jaw-facing surface may then also be referred to as the tissue facing surface, or the basal side or surface of the pontic. The basal surface of the pontic may also be referred to as the tissue facing surface of the pontic.

The phrase "edge" used in relation to a given element, such as the gingival or a dental component or part of such a dental component, may refer to a surface of the element.

In the case of a crown part of the dental component, the jaw-facing surface may be that which faces and engages the corresponding tooth once this has been prepared for accepting the crown. For a crown, the jaw-facing surface may also be referred to as the cervical surface of the crown and/or of the dental component.

The real or virtual surface of the gingival at the locations of the mouth where tooth normally are present may be referred to as the gingival edge. In the context of the present invention, the gingival edge may be the part of a virtually designed or a physical gingival which is to be faced by a jaw-facing surface of the dental component. The jaw-facing surface of a pontic can also be referred to as the basal surface. The jaw-facing surface of a crown may be referred to as the cervical part of the crown.

In the context of the present invention, determining a surface is taken to mean that the surface is virtually generated, e.g. by using curvature based computer implemented algorithms.

In some embodiments, the 3D virtual model of a dental component comprises a dental restoration CAD model.

The virtual preparation may be provided as a "dental preparation CAD model".

An inter-proximal surface of a tooth in the digital 3D representation is a surface on a proximal side of tooth, i.e. a surface which faces a neighboring tooth such that the inter-proximal surface cannot be detected in the 3D scan of the teeth in their pre-prepared configuration.

One advantage of the method for generating a 3D virtual model of a dental component from an obtained digital 3D representation of a pre-prepared set of teeth is that the dental component can be designed before a decision to treat the patient's set of teeth is made and/or before the set of teeth is prepared for the dental component as described in the following example: When the dental component e.g. is a temporary bridge restoration the physical component should preferably be available immediately after the set of teeth is prepared by e.g. preparing teeth for accepting a crown part of the bridge. The 3D virtual model of the dental component should preferably be generated to provide that a physical dental component manufactured from the corresponding virtual model can be arranged in the patient's mouth after the set of teeth has been prepared by extraction of a tooth and/or the preparation of teeth. By virtually removing the relevant teeth of the digital 3D representation of the set of teeth based on a 3D sectioning spline the digital 3D representation can be combined with a virtual diagnostic wax-up showing a desired shape of the teeth of the dental component. The combined model with the digital 3D representation and the virtual diagnostic wax-up can be visualized such that the patient can get an impression of the expected outcome of the dental restorative work before starting the dental restorative work. The combined model may be manufactured by direct digital manufacturing such as 3D printing to provide a physical representation of the target configuration of the teeth. From the combined model the dental component can be designed by e.g. adding virtual preparations and virtual gingival to the digital 3D representation from which the relevant teeth are virtually removed as described herein.

Disclosed is a method for manufacturing a dental component or a physical model of the dental component, where the method comprises:

generating a 3D virtual model of the dental component using the method according to the present invention; and manufacturing the dental component or the physical model of the dental component based on the 3D virtual model by direct digital manufacturing, such as by 3D printing or milling.

Disclosed is a method for manufacturing a combined model for use in planning, visualization and manufacturing of a bridge restoration, where the method comprises:

obtaining a digital 3D representation of a pre-prepared set of teeth showing the region for which the bridge restoration is intended;

providing a virtual diagnostic wax-up for the teeth of the bridge restoration;

generating a 3D virtual combined model by virtually replacing one or more teeth of the digital 3D representation of the pre-prepared set of teeth with corresponding teeth of the virtual diagnostic wax-up; and manufacturing the combined model from the 3D virtual combined model by direct digital manufacturing, such as by 3D printing or milling.

The bridge restoration may be a permanent bridge restoration or a temporary bridge restoration.

The virtual diagnostic wax-up for the teeth of the bridge restoration may comprise at least two crowns surrounding one pontic adapted to replace a tooth which is to be extracted from the set of teeth.

Disclosed is a system for manufacturing a dental component, where the dental component comprises a temporary bridge restoration or a diagnostic wax-up bridge for a region of a patient's set of teeth such that the dental component comprises crowns and at least one pontic, said system comprising a non-transitory computer readable medium having one or more computer instructions stored thereon, where said computer instructions comprises instructions for generating a 3D virtual model of the dental component, where said generating comprises virtually sectioning the part of an obtained digital 3D representation corresponding to the teeth in said region using at least one 3D sectioning spline, determining at least part of the inter-proximal surfaces of the virtually sectioned teeth, and determining a jaw-facing surface for the dental component, where the jaw-facing surface is configured for facing a surface which is not available in the 3D representation; and a manufacturing device configured for manufacturing the dental component from said 3D virtual model.

The system may comprise a scanner device configured for obtaining a digital 3D representation of a set of teeth, such as an intra-oral scanner. The system may comprise a visual display unit and data entry units, such as a computer mouse and a keyboard.

Disclosed is a computer program product comprising program code means for causing a data processing system to perform the method of the present invention when said program code means are executed on the data processing system.

The computer program product may comprise a computer-readable medium having stored there on the program code means.

Disclosed is a method of designing a dental component for at least a region of a patient's set of teeth, wherein the method comprises:
  obtaining a digital 3D representation of at least the region of the patient's set of teeth, where the digital 3D representation is based on a 3D scan, and where the teeth and gingival in the 3D representation are configured to be distinguished from each other;
  virtually designing the dental component;
where at least part of the dental component is designed based on at least a part of the gingival in the 3D representation; and
  obtaining a 3D virtual model of the dental component.

Consequently, it is an advantage that that a dental component, such as a restoration, a temporary, a diagnostic wax-up, and/or such as a part of a restoration, e.g. a pontic in a bridge, can be designed based on the gingival of the 3D representation of the teeth region.

The 3D representation of the teeth may be in the form of a 3D model of the teeth. Thus the 3D representation, e.g. a as 3D model, comprises teeth and gingival. The teeth and the gingival can be distinguished from each other, such as divided, segmented, separated, segregated, split up, detached etc. The distinguishing or separation may be performed by means of the 3D geometry, by means of features in the 3D representation, by means of textural features such as color, surface sensation, feeling, look, appearance, or structures, by means of definition of margin lines and/or other lines or curves etc. The margin lines or other lines or curves may be the lines and curves at the transition between teeth and gingival etc.

In some embodiments the dental component is a restoration, a temporary restoration or a diagnostic wax-up.

In some embodiments the part of the dental component designed based on at least part of the gingival is a crown, a coping, a pontic, a bridge etc.

In some embodiments, the determined jaw-facing surface comprises the jaw-facing surface of the pontic of said dental component, i.e. the basal surface of the pontic.

In some embodiments, the jaw-facing surface comprises the jaw-facing surface of a least one of the crowns of said dental component.

In some embodiments, determining the jaw-facing surface comprises estimating at least a part of the surface which is not available in the 3D representation, such that the jaw-facing surface can be based on the estimated surface.

Estimating the part of a surface which is not available in the 3D may comprise determining the surface, calculating the surface or providing a first approximation of the surface from e.g. a library.

In some embodiments, the method comprises generating a virtual gingival.

In some embodiments, at least a part, such as the basal surface of the pontic of the dental component is designed based on the virtual gingival.

In some embodiments, the basal surface of the pontic is shaped according to the virtual gingival at the position in the digital 3D representation corresponding to where the pontic is to be arranged.

In a pontic, the jaw-facing surface may be designed to follow the gingival below the pontic. This may be provided by designing the basal surface of the 3D virtual model of the dental component to follow the shape of the virtual gingival over at least a part of the jaw-facing surface.

In some embodiments, the virtual gingival is generated based on the digital 3D representation, such as based on the gingival part of the digital 3D representation in the region of said tooth. In some embodiments the method thus comprises designing a virtual gingival based on the gingival in the 3D representation, whereby the dental component may be designed based on the virtual gingival.

The virtual gingival may be generated at the position in the digital 3D representation corresponding to the position at which the pontic is to be arranged when the dental component is arranged in the patient's mouth.

If a digital 3D representation of the set of teeth from which a tooth has been virtually removed and replaced by a virtual gingival and a generated 3D virtual model of a dental component with one pontic are aligned according to their relative arrangement in the patient's mouth, the basal surface of the pontic and the virtual gingival may face each other.

In some embodiments, the 3D sectioning spline for a tooth is adapted to extend over at least one inter-proximal surface of that tooth.

The 3D sectioning spline may be defined automatically using a computer implemented sectioning spline generating algorithm.

In some embodiments, the method comprises manually defining the 3D sectioning spline or manually adjusting an automatically generated 3D sectioning spline.

In some embodiments, manually defining the 3D sectioning spline or manually adjusting an automatically generated 3D sectioning spline is based on sectioning spline control points used to control the shape of the 3D sectioning spline.

In the sectioning of the digital 3D representation, the 3D sectioning spline may be defined to follow the gingival at the tooth or teeth which are being sectioned.

At least a section of the 3D sectioning spline for a tooth may be configured to be shaped according to an expected shape of the margin line that is generated when the tooth is prepared. That is, in both the case where the 3D sectioning spline is automatically generated and when it is defined manually it may be arranged to follow a path along which the operator plans to define the margin line of a tooth.

In some embodiments, the method comprises generating a virtual preparation for the tooth.

The virtual preparation may be defined from the virtual diagnostic wax-up and/or the digital 3D representation of the pre-prepared set of teeth.

The crown part of the dental component can be generated taking into account a virtual preparation of a tooth such that the cervical surface and/or the portion of the crown surface which mates with the prepared tooth are generated from the virtual preparation.

In some embodiments, the boundary of the cervical surface of a crown part of the dental component is derived from said virtual margin line of the corresponding tooth.

In a combined model of the digital 3D representation and a virtual diagnostic wax-up, a boundary of the diagnostic wax-up can be defined from the projection of the virtual margin line onto the virtual diagnostic wax-up. The boundary of the jaw-facing surface of one part of the dental component may be derived from said virtual margin line of said part.

In some embodiments the method comprises generating a virtual margin line for a virtual preparation of at least one tooth in the digital 3D representation. The virtual margin line may be arranged sub-gingival, supra-gingival or along the margin line of the pre-prepared tooth.

The virtual margin line of one or more teeth may be derived from the digital 3D representation of the set of teeth.

In some embodiments, the virtual margin line for a tooth is visualized together with a virtual 3D model of the tooth. The virtual 3D model of the tooth may be provided by the virtually segmenting of the tooth from the digital 3D representation of the set of teeth and the defining of the interproximal surfaces of the tooth.

At least a section of the virtual margin line of a tooth preparation may be substantially aligned with the 3D sectioning spline used for sectioning the corresponding tooth.

In some embodiments the boundary of the jaw-facing surface of one portion of the dental component is derived from said virtual margin line of said portion.

The portion of the dental component may relate to one or more teeth of the set of teeth. For a bridge restoration the dental component is often designed to engage two teeth and replace one or more teeth with pontics.

In some embodiments, the method comprises virtually removing one or more teeth from the digital 3D representation, such as a tooth which is to be replaced by the pontic or a tooth which is to be prepared for accepting a crown. The portion of the digital 3D representation of the set of teeth which is deleted when virtually removing the tooth may be defined and bounded by the 3D sectioning spline.

In some embodiments the method comprises replacing the virtually removed tooth with the virtual preparation in the digital 3D representation of the set of teeth.

In some embodiments, a part of the dental component is designed based on the virtual preparation.

The virtual preparation provides a 3D model of one section of the surface which is not available in the digital 3D representation of the pre-prepared set of teeth, from which surface the jaw-facing surface for a crown part of the dental component may be determined.

It may be advantageous to define the jaw-facing surface of a crown part of the dental component from a virtual preparation of the tooth that the crown part is intended to mate with. When defining the jaw-facing surface from the virtual preparation, the jaw-facing surface may immediately be configured for mating with a tooth prepared according to the virtual preparation.

However, the jaw-facing surface of the crown may also be defined without taking into account a virtual preparation of the tooth. In some embodiments, the jaw-facing surface is defined before a virtual preparation is generated. When a jaw-facing surface has been generated, the virtual preparation may be defined based on this jaw-facing surface.

The virtual gingival provides a 3D model of one section of the surface which is not available in the digital 3D representation of the pre-prepared set of teeth, from which surface the jaw-facing surface for a pontic part of the dental component may be determined.

In some embodiments, the virtual margin line for a tooth is based on the 3D sectioning spline used for sectioning that tooth. It may hence be advantageous that the 3D sectioning spline is made to follow a path which resembles a realistic margin line, such as e.g. a path substantially following the gingival at the tooth.

The virtual gingival may be bounded by the 3D sectioning spline, such that a generated 3D sectioning spline defines the perimeter of the virtual gingival. The shape of the virtual gingival over the surface enclosed by the boundary may be transferred to the jaw-facing surface of the corresponding pontic. The transfer may be such that the jaw-facing surface is shaped substantially as the virtual gingival or modifications may be made to the shape before or after the transfer.

The jaw-facing surface of the pontic may also be defined without taking into account a virtual gingival. In some embodiments, a virtual gingival is generated after the definition of the jaw-facing surface of the pontic e.g. to verify that the shape of the jaw-facing surface meets one or more criteria. When a jaw-facing surface of the pontic has been generated, the virtual gingival may be defined based on this jaw-facing surface.

In some embodiments, the method comprises projecting the virtual margin line onto the portion of the virtual diagnostic wax-up corresponding to that tooth. The generating of the 3D virtual model of the dental component may then be based on this projection. The projection may define the boundary of the jaw-facing surface of the portion of the dental component.

The projection of the virtual margin line onto the virtual diagnostic wax-up may involve an alignment of the virtual diagnostic wax-up and the digital 3D representation of the teeth such that the teeth of the virtual diagnostic wax-up are aligned with the digital 3D representation of the set of teeth. Teeth may be removed virtually and virtual preparations and virtual gingival may be added to the digital 3D representation before or after the alignment. The virtual diagnostic wax-up and the digital 3D representation may intersect at the location where the virtual margin line is intended to be defined such that the projection relates to a registration of the intersection.

The projection of the virtual margin line onto the virtual diagnostic wax-up may be modified manually by an operator to ensure that the dental component is designed according to comply with material or aesthetical requirements.

In some embodiments the method comprises generating a 3D virtual combined model by virtually replacing one or more teeth of the digital 3D representation with teeth according to the virtual diagnostic wax-up.

In some embodiments, the method comprises hole-closure of the combined model such that holes appearing at the location where the diagnostic wax-up and the digital 3D representation connect are closed. With the hole-closure, a so-called watertight combined model may be obtained.

In some embodiments, the method further comprises manufacturing a physical combined model from the 3D virtual combined model by direct digital manufacturing, such as by 3D printing or milling.

In some embodiments the virtual margin line for a tooth, i.e. for the virtual preparation of that tooth, is substantially identical to the 3D sectioning spline for that tooth.

In some embodiments the virtual margin line for a tooth is generated by offsetting the 3D sectioning spline for that tooth. The offset may be along the surface of the tooth towards or away from the occlusal surface of the tooth.

The virtual margin line may enclose a group of teeth comprising two or more teeth, such that the virtual margin line extends over the most distant inter-proximal surface in the group of teeth.

The boundary of the jaw-facing surface of one portion of the dental component may mark the border between the anatomical surface and the jaw-facing of the portion of the dental component.

For a pontic of a bridge restoration, the boundary may comprise a border between the tissue facing surface and the anatomical surface of the pontic. For a crown of a bridge restoration, the boundary may comprise a border between the cervical surface engaging a prepared tooth and the anatomical surface of the crown.

In some embodiments, the virtual margin line for a tooth is configured to extend over the inter-proximal surface of said tooth. This may be advantageous as it provides the option of generating the virtual preparation with a well-defined margin line.

In some embodiments the virtual margin line is defined from the intersection of the virtual diagnostic wax-up and the digital 3D representation of the set of teeth in the combined model.

The jaw-facing surface of one part of the dental component may be derived from said virtual margin line of said part.

In the combined model, the virtual diagnostic wax-up and the digital 3D representation may not intersect over the entire surface of a given tooth in the virtual diagnostic wax-up. This may for instance occur if the 3D sectioning spline is defined on the gingival or when the virtual diagnostic wax-up comprises teeth which are smaller than the original teeth of the patient. In such a situation it may be advantageous to define a boundary of the diagnostic wax-up from the projection of the virtual margin line onto the virtual diagnostic wax-up. This boundary may represent the perimeter of the cervical edge of a crown part or the perimeter of the basal side of a pontic part of the dental component.

In the combined model, holes appearing between the virtual diagnostic wax-up and the digital 3D representation of the set of teeth may be closed using various hole-closing algorithms, and the virtual margin line may be determined in least in part from the surface formed to close these holes.

The digital 3D representation from which teeth are virtually removed and replaced by virtual preparations and virtual gingival, can be virtually aligned with the virtual diagnostic wax-up. The resulting combined model can be visualized on a computer screen such that an operator can define the virtual margin line from the visualization. The intersections can also be derived using computer based algorithms. Holes in the combined model can also be visualized and identified in this way.

In some embodiments, the virtual margin line is automatically defined. The automatic definition of the virtual margin line may be based on computer implemented algorithms configured for identifying structures in a virtual model, such as the transition between tooth surface and gingival in a virtual model of the patient's set of teeth.

In some embodiments the virtual margin line is manually defined or wherein a section of an automatically generated virtual margin line is adjusted manually.

In some embodiments at least one anatomical surface of the 3D virtual model of the dental component is derived from the shape of the teeth in the pre-prepared configuration. The shape of the teeth in the pre-prepared configuration may be as seen in the digital 3D representation.

In some embodiments at least one anatomical surface of the 3D virtual model of the dental component is derived from the shape of the teeth in the virtual diagnostic wax-up.

In some embodiments the method comprises visualizing at least one virtual preparation using a visual display unit, such as a computer screen.

In some embodiments, the method comprises trimming the digital 3D representation of the set of teeth.

Trimming of the digital 3D representation can be realized by deleting data points from the digital 3D representation and/or by smoothing surfaces if the digital 3D representation. The trimming may be configured to provide that the manufacturing of a physical model of the set of teeth is made easier and/or that it can be manufactured using less material.

In some embodiments the inter-proximal surfaces are generated using polynomial algorithms to provide a realistic presentation of these surfaces.

In some embodiments the method comprises determining a target insertion direction for the dental component. The target insertion direction can be determined by an operator using e.g. a pointing tool, such as a computer mouse, to manipulate a representation of the insertion direction relative to the digital 3D representation of the set of teeth or relative to the combined model.

In some embodiments, the 3D virtual model of the dental component is generated taking into account the target insertion direction for the dental component. For a crown part of a dental component, the target insertion direction can be taken into account by arranging e.g. the cervical surface of the crown such that undercuts are avoided.

In some embodiments the virtual preparation is shaped according to this insertion direction.

The orientation and location of the preparations may be important especially for dental components such as a bridge where the two crowns must be capable of being inserted simultaneously.

In some embodiments, the crown parts of the dental component are shaped according to an egg-shell configuration.

In the egg-shell configuration thickness of the crown's shell is substantially constant over the major part of its surface. The egg-shell configuration has the advantage due to the large void inside the tooth, the requirements to the precision of the preparation of the teeth is reduced.

In some embodiments, the method is computer-implemented or at least a number of the steps of the method are computer-implemented.

In some embodiments the method comprises modifying the digital 3D representation of the set of teeth by virtually replacing one or more teeth of the digital 3D representation with virtual preparations, and generating the 3D virtual model of the temporary bridge restoration with the crown parts corresponding to the prepared teeth. The 3D virtual model of the temporary bridge restoration may be generated at least partly from the virtual diagnostic wax-up.

In some embodiments, the method comprises manufacturing a physical model from the modified digital 3D representation of the set of teeth and/or the 3D virtual model of the temporary bridge restoration by direct digital manufacturing, such as by 3D printing or milling. The result of this may be a physical model with virtual preparations and a separately milled temporary bridge restoration, where these can be used for visualizing an expected outcome of the restorative work.

In some embodiments, the method comprises confirming the occlusion of the set of teeth when the dental restoration is arranged at the teeth.

If a patient wishes to have a dental restoration, he will see a dentist. The patient may wish to have his teeth restored, if he for example has a broken tooth. In the first visit at the dentists, the dentist may perform an intra oral scanning in the patient's mouth or the dentist may take an impression of the mouth. The impression may then be scanned, or a model may be casted from the impression, and then the model may be scanned. The 3D scanning, either the intra oral scanning, the scanning of the impression or model, will provide a digital 3D representation also known as a 3D virtual or digital model of the patient's teeth. Based on this 3D virtual model, e.g. a dental technician may design a temporary prosthesis, e.g. a temporary bridge, and the temporary prosthesis may be manufactured. At the second visit at the dentist, the dentist for example removes the broken tooth and prepares the two neighbor teeth by grinding them so that a crown in a bridge can be attached to each of the prepared teeth. The dentist then again performs e.g. an intra-oral scanning or takes an impression for capturing the patient's teeth after the removal of the broken tooth and after the preparation of the neighbor teeth. The temporary prosthesis in the form of e.g. a bridge can then be attached temporarily on the two prepared teeth and in between the crowns a pontic is present which replaces the broken tooth. If an impression is made, the impression is scanned or the model created from the impression is scanned. The scanning, either the intra oral scanning, the scanning of the impression or model, will provide a 3D virtual or digital model of the patient's teeth. Based on this 3D virtual model, e.g. a dental technician may design a permanent/lasting/final prosthesis, e.g. a permanent bridge, and the permanent prosthesis may be manufactured. At the third visit at the dentist, the dentist removes the temporary prosthesis and attaches the permanent prosthesis in the patient's mouth. The prosthesis may be a bridge which can be attached permanently on the two prepared teeth and in between the crowns a pontic is present which replaces the broken tooth. The place of the broken tooth may be called the extraction wound.

The gingival may fall down into the extraction wound or be disrupted when a tooth is gone, removed, cut down etc., and thus a temporary is designed such that the mouth/smile of the patient looks nice when the temporary is worn and before the real/final restoration is produced and arranged. Thus the temporary may be designed such that it covers or fits to the gingival which has fallen into the extraction wound or has been disrupted. Thus the pontic part of the temporary may be bigger than usual because of the extraction wound or hole and because the gingival has falling down into it.

Over time the bone under the gingival will build up again, and for the final restoration the pontic part may thus not need to be so big.

The method relates to restorations and prosthesis, e.g. temporaries, and to prostheses for the gingival.

In some embodiments the method comprises designing the edge of the dental component adjacent to the gingival part.

In some embodiments the method comprises designing the virtual gingival by using one or more planes or curves.

In some embodiments the method comprises designing the virtual gingival to be convex or concave in shape. The virtual gingival may be designed to have a convex or concave shape along and/or perpendicular to the dental arch.

In some embodiments the method comprises designing the virtual gingival by means of a gingival template, i.e. the virtual gingival is selected from a library of gingival profile templates.

In some embodiments, the virtual gingival is generated by freeform modeling using flexible sculpt tools. An operator may for example use a computer pointing tool, such as a computer mouse, to adjust the shape of a virtual 3D model of the virtual gingival by changing the relative positions of control points used to control the shape of the virtual 3D model.

In some embodiments the gingival template comprises at least three points configured for sculpting the gingival.

In some embodiments the selected virtual gingival is modified to fit the patient's set of teeth.

When the virtual gingival is adapted to replace a virtually removed tooth in the digital 3D representation of the set of teeth, the virtual gingival may be adapted to close the hole in the digital 3D representation resulting from the virtual removal of the tooth.

In some embodiments the method comprises virtually removing a tooth from the 3D representation, where the tooth is positioned in the place where a pontic of the dental component is configured to be arranged. The part of the digital 3D representation corresponding to the tooth may be identified by the 3D sectioning spline.

In some embodiments the method comprises virtually removing the tooth before designing the virtual gingival.

In some embodiments the method comprises replacing the virtually removed tooth with the virtual gingival, in the digital 3D representation of the set of teeth.

In some embodiments, the method comprises providing a diagnostic wax-up for the teeth of the dental component.

In some embodiments, the dental component is a temporary restoration bridge and the method comprises providing a diagnostic wax-up for the teeth of the temporary restoration bridge.

In some embodiments the method comprises virtually arranging a pontic in the place of a tooth.

In some embodiments the method comprises defining a gap between the edge of the pontic and the adjacent gingival. This gap may be denoted as the basal gap.

The traditional way of making temporary restorations or prosthesis for a patient may comprise taking an impression of the teeth, casting a physical model of the teeth from the impression, preparing the broken tooth on the physical model, and building up the temporary on the model. This method is very time consuming, and the final design of the restoration cannot be made using the temporary design. Alternatively, the dentist can build up the temporary directly in the mouth of the patient. This method may be faster, but it may be very uncomfortable for the patient to have the temporary build up in his mouth, and again the final design of the restoration cannot be made using the temporary design. Thus when making the final design, the dental technician has to start all over as he cannot reuse the design he already made for the temporary restoration.

Disclosed is a computer-implemented method of designing a dental component for a region on a patient's set of teeth, wherein the method comprises the steps of:

obtaining a digital 3D representation of at least the region of the patient's set of teeth, where the digital 3D representation is based on a 3D scan;

determining at least part of a surface which is not available in the 3D representation;

virtually designing a preparation in the region of the patient's set of teeth for the dental component; and obtaining a 3D virtual model of the dental component.

Consequently, it is an advantage that a virtual preparation is designed, whereby a real preparation of the tooth or teeth is not performed, before the patient has accepted the design of both the dental component e.g. a restoration, and of the preparation to be performed. Thus it is an advantage that the patient can see a virtual design of the preparation and of the dental component, before having the preparation made.

Furthermore, it is an advantage that a 3D representation produced from a 3D scan of the relevant region can be used to design a virtual preparation for the relevant region. This ensures that the virtual preparation will actually fit to the real case, if the virtual preparation is used to perform a physical preparation on a tooth or teeth in the patient's mouth.

Often there are surfaces of the teeth that the 3D scan cannot capture, such as a proximal side of tooth or a sub-gingival part of a tooth, and it is an advantage that these surfaces can be determined, calculated, and/or estimated and thus used in designing the preparation, and/or the dental component, such as a restoration, a temporary restoration or a diagnostic wax-up etc. Thus the surface may be a surface of a tooth. Determining at least part of a surface which is not available in the 3D representation may also mean that it is a surface that does not exist, and thus the determination of a surface may means the designing of a surface, such as the designing of the dental component.

The surface which is not available in the 3D representation may not be present in the pre-prepared set of teeth, that is the surface does not exist when the 3D scan of the set of teeth is obtained, For instance in the case where a dead or damaged tooth is to be extracted to provide space for a pontic of a bridge, the surface will first appear after the tooth has been extracted. The surface which is not available in the 3D representation may also be the surface that emerges after the gingival is healed after the extraction of a tooth.

Referring to a surface as not being available in the digital 3D representation does not exclude that the surface is generated to become part of the digital 3D representation by generating e.g. a virtual gingival. The phrase may refer to the situation where the surface could not be detected in the 3D scan, such as when the surface did not exist when the 3D scan was performed.

In prior art there may be no sub-gingival information of the tooth, no surface extrapolation of un-known surfaces, no design based on a CAD drawing or design of a new teeth, no morphing from a virtual design but only morphing from the 3D scan, and only changes made to the outside shape of scan etc.

The present invention may relate to virtually designing a preparation, not performing the real preparation.

The patient's teeth before any treatment has been applied can be denoted pre-prepared teeth. However, the pre-prepared teeth may also be the patient's teeth prior to the preparation work that is often required prior to a dental restoration. Therefore the pre-prepared teeth may have received some, typically minor, treatment, such as cleaning, polishing, minor grinding and/or the like, but the pre-prepared teeth have not been prepared for a dental restoration. A preparation for a dental restoration typically requires grinding, drilling, removal, endodontic treatment and/or the like, of relevant tooth/teeth.

The phrase pre-prepared teeth may also be used in relation to a set of teeth wherein dental work has already been made on the teeth that are not part of said region, i.e. the dental component may have been made already have been prepared in earlier dental work on the patient's other teeth.

The phrase pre-prepared configuration of the set of teeth is also used in this application in relation to pre-prepared teeth.

It is an advantage of the present invention that many different kinds of information, such as scan data, 3D CAD design may be used to design and finally obtain a 3D virtual model of a dental component to be inserted or arranged in the mouth of a patient, either temporarily or permanently.

Determining at least part of a surface and/or designing a feature comprises determining and/or designing the shape of the surface.

The virtual designs may be CAD designs.

The steps of the method may be performed wholly or partly by an operator or user and/or wholly or partly performed automatically by the processing means of a computer program.

The diagnostic component can e.g. be a restoration produced because a tooth is broken, missing, should be "turned" etc.

Thus in some embodiments determining at least part of a surface not available in the 3D representation comprises virtually designing at least a part of the dental component.

In some embodiments the surface which is not available in the 3D representation is at least a part of the dental component being designed.

In some embodiments the surface which is not available in the 3D representation is an existing part of patient's set of teeth.

In some embodiments determining at least part of a surface which is not available in the 3D representation comprises determining a proximal side of a tooth.

In the context of the present invention, the phrases "proximal side of a tooth" and inter-proximal surface of a tooth are used interchangeably.

In some embodiments determining at least part of a surface which is not available in the 3D representation comprises determining a sub-gingival tooth part.

A sub-gingival determination or extrapolation may be particularly relevant to obtain when designing crowns or temporary crowns.

In some embodiments determining at least part of a surface which is not available in the 3D representation is based on the 3D representation.

In some embodiments determining at least part of a surface which is not available in the 3D representation is based on the shape of neighbor teeth, and/or based on a default restoration.

In some embodiments determining at least part of a surface which is not available in the 3D representation is based on estimation by extrapolation of the 3D representation of the tooth.

In some embodiments the virtual design of at least part of dental component and/or of the preparation is based on at least part of the surface which is not available in the 3D representation.

In some embodiments the preparation is designed first, and at least part of the dental component is then designed based on the preparation.

In some embodiments the dental component is automatically derived when the preparation is designed.

In some embodiments at least part of the dental component is designed first, and the preparation is then designed based on the at least part of the dental component.

In some embodiments the preparation is automatically derived when at least part of the dental component is designed.

In some embodiments the preparation is designed or derived from the internal part of the dental component, such as the internal part of a crown.

In some embodiments the dental component is a restoration and/or a temporary restoration and/or a diagnostic wax-up.

A diagnostic wax-up may be produced for showing the patient how the new teeth will look before the actual preparation of his teeth. A temporary or a temporary restoration is worn by the patient after the preparation is done and before the real or permanent restoration has been produced.

A diagnostic wax-up may be particularly relevant when designing e.g. veneers, and for designing veneers subgingival surface information or extrapolation may not be used.

In some embodiments the temporary restoration and/or restoration is a crown, a bridge, an implant and/or a veneer. A crown may also be denoted a coping. A veneer or veneering may be made on a coping.

In some embodiments the crown comprises an internal part and an external part. The internal part of the crown may be denoted a coping.

In some embodiments the shape of the internal part of the crown is equal to the shape of the preparation.

In some embodiments a cement space is defined between the internal part of the crown and the preparation.

In some embodiments the method further comprises designing structures in the inside surface of the crown.

It is an advantage that the inside surface of the crown, the internal part of the crown and/or the coping comprises structures, because by means of the structures the crown may be attached better, easier, faster, and/or more robust to the preparation when gluing or cementing the crown on the preparation. The structures may also be denoted retention grids.

In some embodiments the structures are shaped as grooves.

The grooves may be vertically relative to the insertion direction of the crown. It is an advantage to provide vertical grooves in the inside surface, since vertical grooves may be easy to manufacture, both for a person and for a machine, such as milling machine or a 3D printer. Furthermore vertical grooves may provide a good attachment to the surface of the preparation.

In some embodiments the method further comprises determining and visualizing a virtual margin line.

The virtual margin line may relate to one or more teeth in the set of teeth.

In some embodiments the method further comprises determining the virtual margin line from the 3D representation of the region of the patient's set of teeth.

In some embodiments the method further comprises arranging the virtual margin line to lie on the determined surface which was not available in the 3D representation.

In some embodiments the method further comprises connecting the virtual preparation with relevant available and/or estimated parts of a tooth in the region of the patient's set of teeth.

In some embodiments the method further comprises virtually snapping the preparation to the surface of the least one tooth in the region of the patient's set of teeth.

In some embodiments the preparation design is free-form designed, designed based on the original tooth shape, designed based on the design of the dental component such as a crown, is a default design, is a parametric or algorithmic design, and/or is from a library.

In some embodiments the preparation design is based on which kind of tooth that is to be prepared, such as a molar tooth, a premolar tooth, or an anterior tooth.

In some embodiments the method further comprises designing the internal and/or external part of the crown based on the original tooth in the region of the patient's set of teeth.

In some embodiments the dental component is adapted to be attached in the region on the patient's set of teeth, after a physical preparation is performed on at least one tooth in the region on the patients' set of teeth.

In some embodiments the method further comprises determining a preparation guide for the dentist prior to preparing the teeth.

The preparation guide may also be denoted or comprise a drill guide.

In some embodiments the method further comprises performing a virtual segmentation of at least part of the set of teeth.

The virtual segmentation may be performed for easy handling of neighbor teeth.

In some embodiments the method further comprises virtually cutting out the at least one tooth in the region of the patient's set of teeth.

In some embodiments the method further comprises determining an insertion direction of the at least one tooth in the region of the patient's set of teeth.

In some embodiments the dental component is a temporary restoration, and the method further comprises designing a final restoration based on the design of the temporary restoration.

Thus the first dental component may be designed according to the method(s) disclosed above and may be e.g. a temporary restoration. The second dental component may then be a final restoration. Thus the final restoration is based directly on the design of the temporary restoration.

This is an advantage, because the method enables dental laboratories to save time and materials costs. Furthermore it is an advantage that the method is fast, easy and provides consistent designs because final restorations, such as crowns, are actually based on the previously designed temporary/ies.

In some embodiments the method further comprises transferring the design of the temporary restoration into a design of a final restoration by means of aligning the design of the temporary restoration with a 3D representation based on a 3D scan of the patient's prepared teeth.

In some embodiments the temporary design is modified prior to the transfer.

In some embodiments the temporary design is a one-layer design, and wherein the one-layer temporary design is converted to a two-layer restoration design.

In some embodiments the method further comprises performing validation scanning in the mouth of the patient with an intra-oral scanner while performing the preparation procedure according to the virtual design for validating that the preparation is performed correct according to the preparation guide.

It is an advantage that the dentist can perform a validation of the physical preparation he is performing in the tooth or teeth of the patient by using an intra-oral scanner simultaneously or concurrently with the preparation procedure. He can scan a region where he has been preparing a tooth and by comparing the scan of this region with the preparation guide, e.g. software model or instructions, the dentist can see if he has cut away enough material of the tooth or if he needs to cut away some more material and where on the tooth the material should be removed from. This intra oral scanning validation can be an alternative and/or an addition to using physical preparation guides.

In some embodiments the validation scanning provides a real time validation.

In some embodiments the 3D scan is an intra oral scan of at least part of the patient's set of teeth, a scan of at least part of an impression of the patient's set of teeth, and/or a scan of at least part of a model of the patient's set of teeth.

In some embodiments the 3D scan is performed by means of laser light scanning, white light scanning, probe-scanning, X-ray scanning, and/or CT scanning.

The 3D scan may provide data arranged as a point cloud from which the surface of the set of teeth can be reconstructed. The reconstruction of the surface may be performed using a triangulation technique.

An example of a work flow may be:
a) in a dentist clinic a patient is e.g. intra orally scanned or an impression is taken which is then scanned.
b) in a dental lab the virtual preparation is designed based on the scan and the restoration is CAD designed based on the virtual preparation.
c) in the dentist clinic the virtual preparation and the restoration are presented to the patient and if the patient accepts them, the preparation guide is visualized and used to perform the preparation. A temporary restoration may be placed on the preparation until the restoration has been produced and inserted in the patient's mouth.

Another example of a work flow may be:
a) an estimated sub-gingival tooth part is based on the scan of a tooth.
b) a margin line is set based on the estimated sub-gingival tooth part.
c) a virtual preparation is designed based on the margin line
d) a temporary is designed, the temporary crown is extracted from the CAD design and a prep guide is also determined.

Another example of a work flow may be:
a) a digital 3D representation is obtained from a 3D scan.
b) the relevant tooth of the scan is virtually cut out, i.e. the tooth is virtually removed from the digital 3D representation.
c) non-available parts of the tooth is extrapolated, e.g. proximal sides and/or sub-gingival part.
d) the virtual preparation is designed based on the extrapolated parts, or the restoration or temporary restoration is designed, e.g. a crown.
e) the virtual preparation is connected with relevant parts of the tooth.
f) the internal and/or external side of the crown is designed based on the existing tooth.
g) a preparation guide is performed.

Another example of a work flow may be:
a) a preparation or at least part of crown or an internal surface of a crown is placed in the virtual space using the graphical user interface (GUI).
b) the margin line is determined based on one of the features.

Another example of a work flow may be:
a): obtain a digital 3D representation of the pre-prepared set of teeth e.g. by inter-oral scanning;
b) virtually remove relevant teeth from the digital 3D representation;
c): create a virtual diagnostic wax-up for the set of teeth, said virtual diagnostic wax-up comprising one or more virtual dental restorations, such as crowns or a bridge
d) combine the digital 3D representation of the teeth from which teeth are virtually removed with the diagnostic wax-up, such as combining by virtually replacing one or more teeth of the digital 3D representation with teeth according to the virtual diagnostic wax-up. The virtual combined model may also be referred to as a virtual diagnostic lab model and it can show a target dental situation for the patient;
e) hole-closure of the combined model such that holes appearing at the location where the diagnostic wax-up and the digital 3D representation connect may be closed. The hole-closing may be performed using a curvature based hole-closure algorithm.
f) adding to the combined model a virtual preparation to the part of the digital 3D representation where a corresponding tooth has been virtually removed. This can be advantageous in case the dental technician chooses to design the digital temporary restoration from the shape of the virtual preparation.

The work flow may further comprise:
g): finalizing the virtual diagnostic lab model by e.g. adding a virtual base to the virtual combined model;
h): manufacture a physical diagnostic lab model from the virtual diagnostic lab model.

When some of these workflows are combined their order may be as above or in a different order.

A preparation guide may be a recommended procedure to execute a dental preparation. It may be in the form of documents, audiovisual material, or physical artifacts such as example dental models. It may contain information concerning which equipment to use and how to use it. Thus a preparation guide is typically directed at a dentist, a dental technician, a dental lab and/or the like. A preparation guide may comprise instructions, e.g. software instructions that can be executed by a machine used for the preparation.

In some embodiments of the invention the software assists the dentist with the preparative work. In many cases, general preparation guides are provided by manufacturers of dental material and equipment. To ease the dentist's work and to improve the restorative strength and overall quality, the method may provide the preparation guides automatically for the particular dental component design, e.g. of a restoration.

Possibly, the software can assist with planning crown lengthening. In this context, for example the margin can be prevented from being placed too sub-gingivally. Also the type of margin, e.g. bevel or shoulder, could be suggested by the software.

Besides proposing details of the preparation, the software that generates a preparation guide can possibly also validate a preparation that the dentist and/or dental technician have devised by other means. For example, the software can evaluate restorative strength and/or choice of materials, and/or even the choice of restorative treatment method.

The preparation guide can take many forms including instruction text, multiple 2D screen shoots, 3D animations, computer visualization, videos and/or instructions for machined/robot preparation. A preparation guide may also include a physical model of the desired, positive, preparation, or a physical negative representation which can be tested in the mouth of the patient. For example in the case where the model is a scanned cast model, the dental technician could prepare this cast. Because the virtual preparation is also available in digital form, the dental preparation CAD model, it could also be manufactured by CAM.

A further embodiment comprises the step of providing a preparation guide for the dentist prior to preparing the teeth, said preparation guide preferably at least partly based on the dental preparation CAD model.

In a further embodiment said preparation guide provides assistance in relation to lengthening of crown(s), location and/or type of the margin, and/or the like, and wherein the generation of said preparation guide is at least partly based on the dental restoration CAD model and/or the 3D model of the pre-prepared teeth and/or the dental preparation CAD model and/or segmentation of said models.

In a further embodiment said preparation guide comprises instructions for execution of a machine generated preparation and/or preparation model.

In a further embodiment said preparation guide comprises a dental model of the preparation, such as a gypsum model and/or a wax-up model, such as a marked-up dental model.

In a further embodiment aligning is at least partly based on detecting and/or demarcating and/or aligning margin lines of the models.

In a further embodiment transferring the design of the dental restoration CAD model comprises morphing part of the dental restoration CAD model to the 3D model of the prepared teeth.

In a further embodiment morphing is applied near the margin line of the dental restoration CAD model and/or the 3D model of the prepared teeth.

In a further embodiment the impact of morphing is highest near the margin line of the dental restoration CAD model and/or the 3D model of the prepared teeth, with decreasing impact of the morphing when increasing the distance to the margin line.

In a further embodiment, the step of transferring the design of the dental restoration CAD model comprises creating an inner surface of the dental restoration CAD model as an offset to the 3D model of the prepared teeth, said offset preferably in the occlusal and/or incisal direction from the margin line of the 3D model of the prepared teeth.

In a further embodiment comprises said offset is provided automatically.

In a further embodiment comprises a significant part of the outer surface of the dental restoration CAD model is maintained when transferred to the 3D model of the prepared teeth, the contour of the inner surface of the dental restoration CAD model is substantially similar to the outer surface of the 3D model of the prepared teeth and the margin line area of the dental restoration CAD model and the 3D model of the prepared teeth are morphed together.

Yet a further embodiment comprises the step of transferring the design of the dental restoration CAD model comprises morphing the dental preparation CAD model with the 3D model of the prepared teeth, thereby providing a transformation of the dental preparation CAD model to the 3D model of the prepared teeth, and subsequently applying this transformation to the dental restoration CAD model.

A further embodiment comprises the step of modifying the design of the dental restoration CAD model subsequent to the step of transferring said dental restoration CAD model to the 3D model of the prepared teeth.

The present invention relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for designing a dental component for at least a region of a patient's set of teeth, wherein the system comprises:
 means for obtaining a digital 3D representation of at least the region of the patient's set of teeth, where the digital 3D representation is based on a 3D scan, and where the teeth and gingival in the 3D representation are configured to be distinguished from each other;
 means for virtually designing the dental component; where at least part of the dental component is designed based on at least a part of the gingival in the 3D representation; and
 means for obtaining a 3D virtual model of the dental component.

In particular, disclosed herein is a system for designing a dental component for a region on a patient's set of teeth, wherein the system comprises:
 means for obtaining a digital 3D representation of at least the region of the patient's set of teeth, where the digital 3D representation is based on a 3D scan;
 means for determining at least part of a surface which is not available in the 3D representation;
 means for virtually designing a preparation in the region of the patient' set of teeth for the dental component; and
 means for obtaining a 3D virtual model of the dental component.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 2a through 2g show examples of designing a virtual preparation and designing at least part of a dental component.

FIGS. 10a through 10h show an example of designing at least a part of a dental component based on a gingival part.

DETAILED DESCRIPTION

In the following description, reference is made to the accompanying figures, which show by way of illustration how the invention may be practiced.

Figure 1:
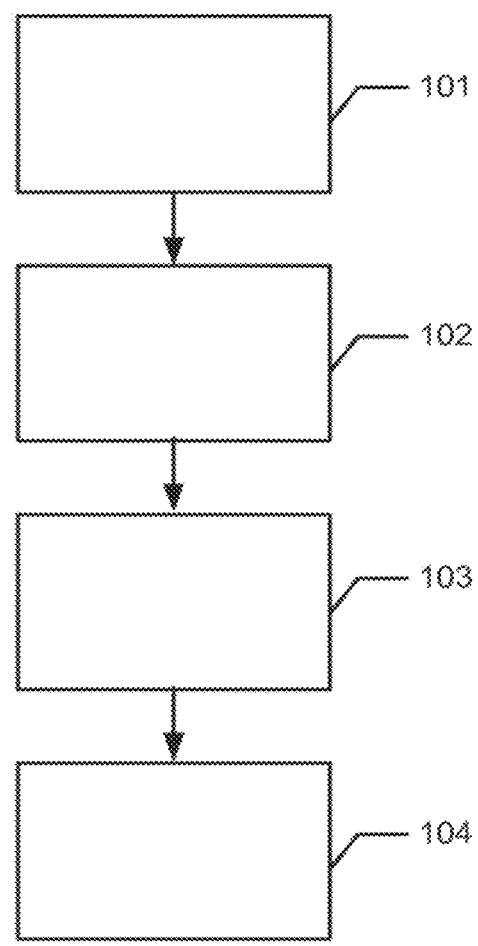
FIG. 1 shows an example of a flowchart of the computer-implemented method.

FIG. 1 shows an example of a flowchart for an embodiment of the method of designing a dental component for a region on a patient's set of teeth.

In step 101 a digital 3D representation of at least the region of the patient's set of teeth is provided. The digital 3D representation is based on a 3D scan.

In step 102 at least part of a surface which is not available in the 3D representation is determined.

In step 103 a preparation is virtually designed in the region of the patient' set of teeth for the dental component.

In step 104 a 3D virtual model of the dental component is obtained.

The order of the steps may be the order as above or a different order, e.g.: In step 101 a digital 3D representation of at least the region of the patient's set of teeth is provided. The digital 3D representation is based on a 3D scan.

In step 102 a preparation is virtually designed in the region of the patient' set of teeth for the dental component.

In step 103 at least part of a surface which is not available in the 3D representation is determined.

In step 104 a 3D virtual model of the dental component is obtained.

However, other orders may also be possible.

Determining at least part of a surface not available in the 3D representation may comprise virtually designing at least a part of the dental component. Thus then the surface which is not available in the 3D representation may be at least a part of the dental component being designed.

Alternatively and/or additionally, the surface which is not available in the 3D representation may be an existing part of patient's set of teeth. Thus determining at least part of a surface which is not available in the 3D representation may comprise determining a proximal side of a tooth, and/or a sub-gingival tooth part.

FIG. 2 shows examples of designing a virtual preparation and designing at least part of a dental component.

Figure 2A:
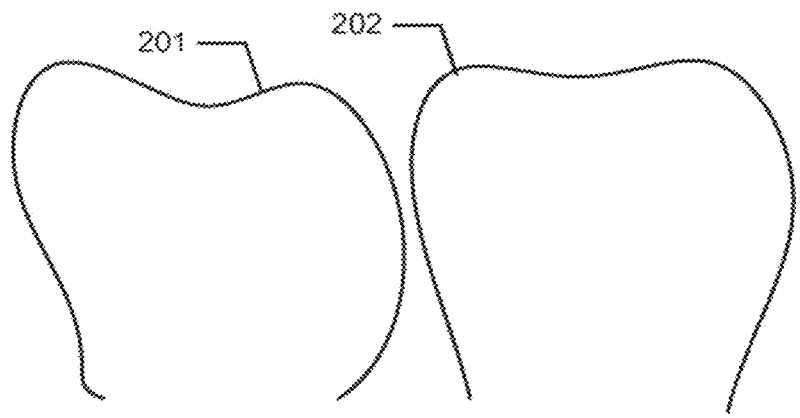

FIG. 2a) shows an example of a digital 3D representation. Even though the representation only appears to be a 2D representation, it is intended to illustrate a digital 3D representation for this purpose. The digital 3D representation shows two teeth 201, 202 from a set of teeth of a patient.

Figure 2B:
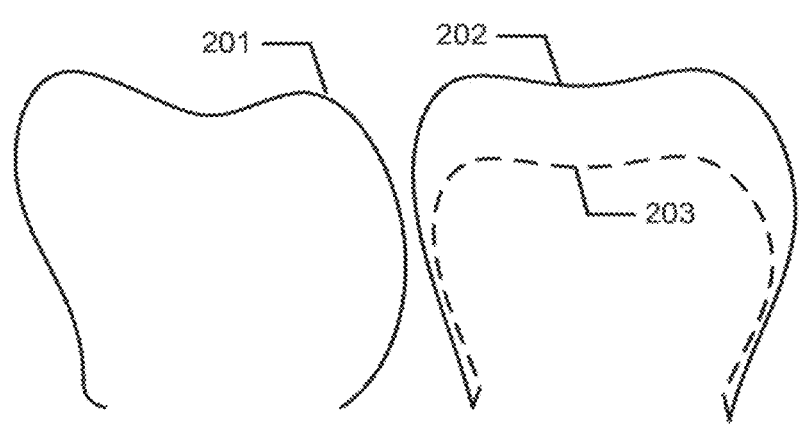

FIG. 2b) shows an example of a virtual preparation 203 or of virtually preparing or prepping the tooth 202.

Figure 2C:
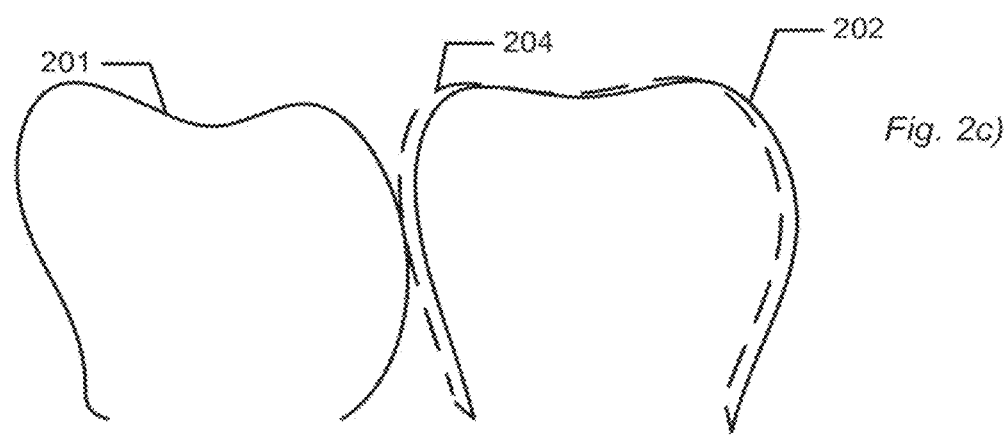

FIG. 2c) shows an example of virtually designing at least part of a dental component. In this case a crown 204 is designed.

Both the virtual preparation 203 and the crown 204 can be designed based on the original shape of the tooth 202.

FIG. 2d) shows an example where the virtual design of a crown 204 is designed first, and then the virtual design of the preparation 203 is designed afterwards. The virtual design of the preparation 203 may thus be based on the shape of the original tooth 202 and/or based on the virtual design of the crown 204.

Figure 2E:
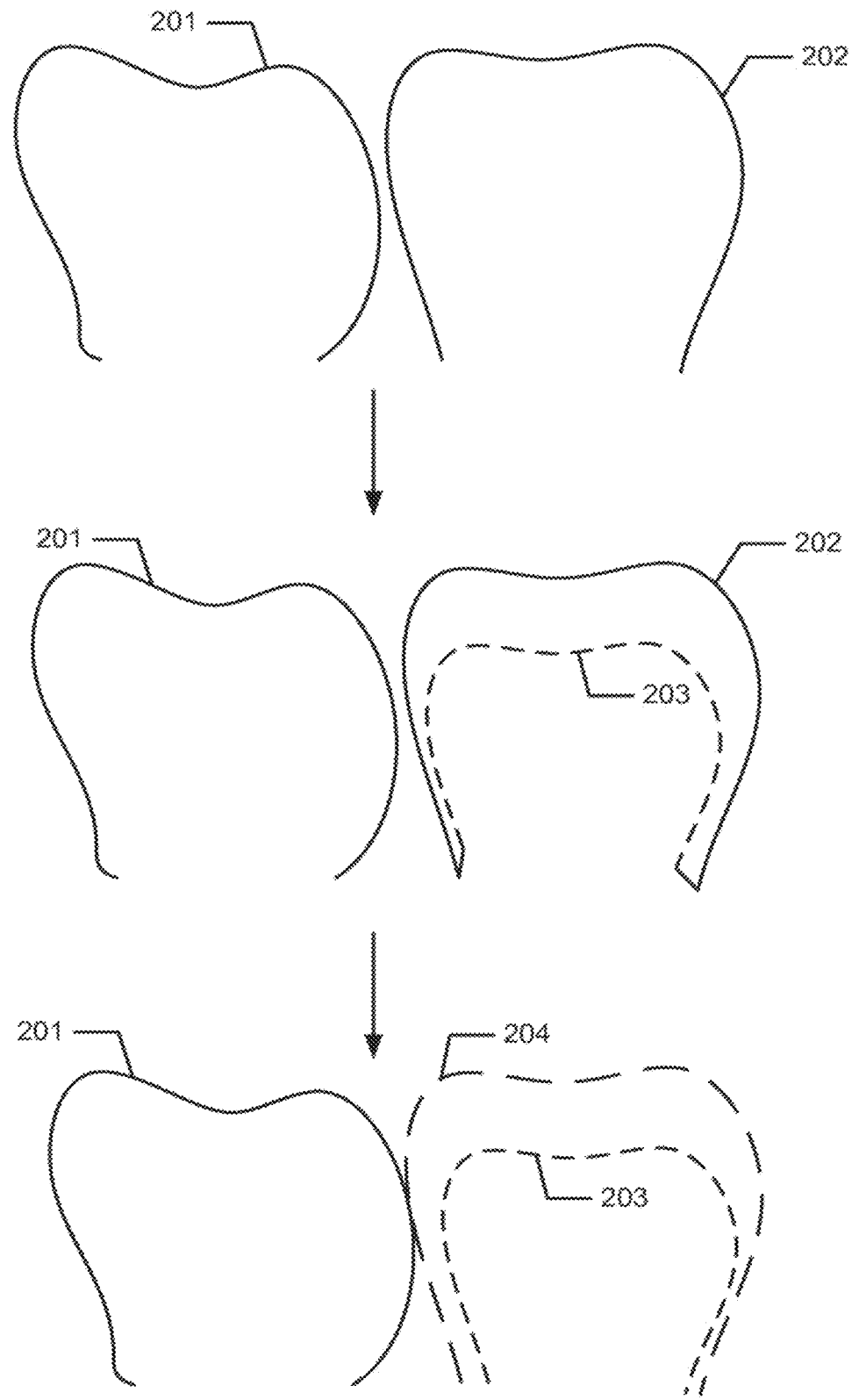

FIG. 2e) shows an example where the virtual design of the preparation 203 is designed first, and then the virtual design of the crown 204 is designed afterwards. The virtual design of the crown 204 may thus be based on the shape of the original tooth 202 and/or based on the virtual design of the preparation 203.

FIG. 2f) shows an example where the virtual design of a crown 204 is designed first, the original tooth 202 is then ignored, and finally the virtual design of the preparation 203 is designed afterwards. The virtual design of the preparation 203 may thus be based on the virtual design of the crown 204, but may not be based on the shape of the original tooth 202.

FIG. 2g) shows an example where the virtual design of the preparation 203 is designed first, the original tooth 202 is then ignored, and finally the virtual design of the crown 204 is designed afterwards. The virtual design of the crown 204 may thus be based on the virtual design of the preparation 203, but may not be based on the shape of the original tooth 202.

Ignoring the original tooth 202 may comprise deleting the tooth 202, and/or ignoring the tooth 202 may be implemented by fading the tooth 202 such that it is less apparent than the other features/shapes.

FIG. 3 shows an example of determining a part of a surface which is not available in the 3D representation.

Figure 3A:
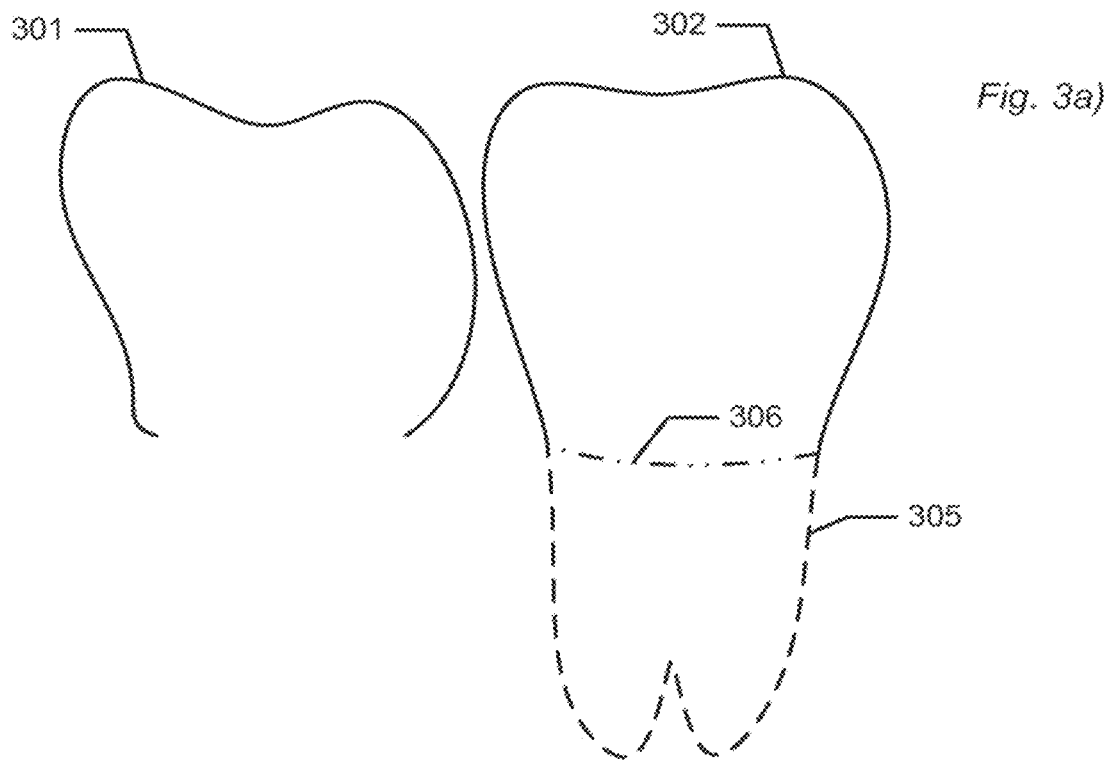
FIGS. 3a and 3b show an example of determining a part of a surface which is not available in the 3D representation.

FIG. 3a) shows an example where the sub-gingival tooth part 305 of the tooth 302 is determined. The margin line 306 is also determined. The sub-gingival tooth part 305 is not available in the scan, when scanning using laser light, since this type of scanning cannot scan through the gingival tissue. Thus the sub-gingival tooth part 305 may be determined by extrapolating the available 3D representation of the surface of the tooth 302.

Figure 3B:
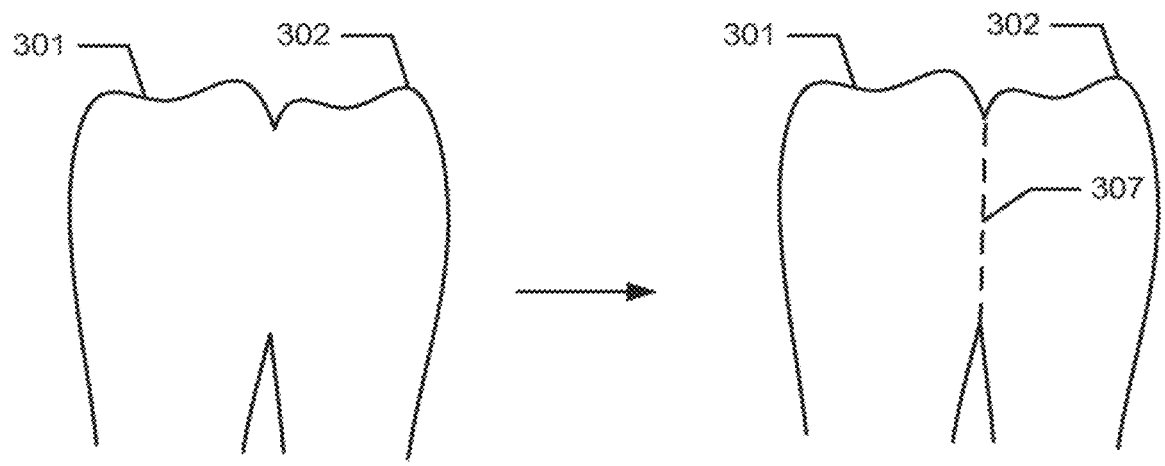

FIG. 3b) shows an example of determining a proximal side 307 of the tooth 302. The left figure shows that the proximal side of a tooth 302 may be impossible to represent in a 3D scan, because the teeth 301 and 302 lie very close together so that there is no space between them. In the digital 3D representation the actual proximal side of the tooth 302 is therefore not available. The right figure shows that the proximal side 307 of the tooth 302 may be determined by extrapolating the available digital 3D representation of the surface of the tooth 302. The available digital 3D representation of the surface of the neighbor tooth 301 may also be used in determining the proximal side 307 of the tooth 302.

The extrapolations may comprise any kind of extrapolation, such as linear extrapolation, polynomial extrapolation, conic extrapolation, french curve extrapolation, a combination of two or more different extrapolations etc.

Figure 4:
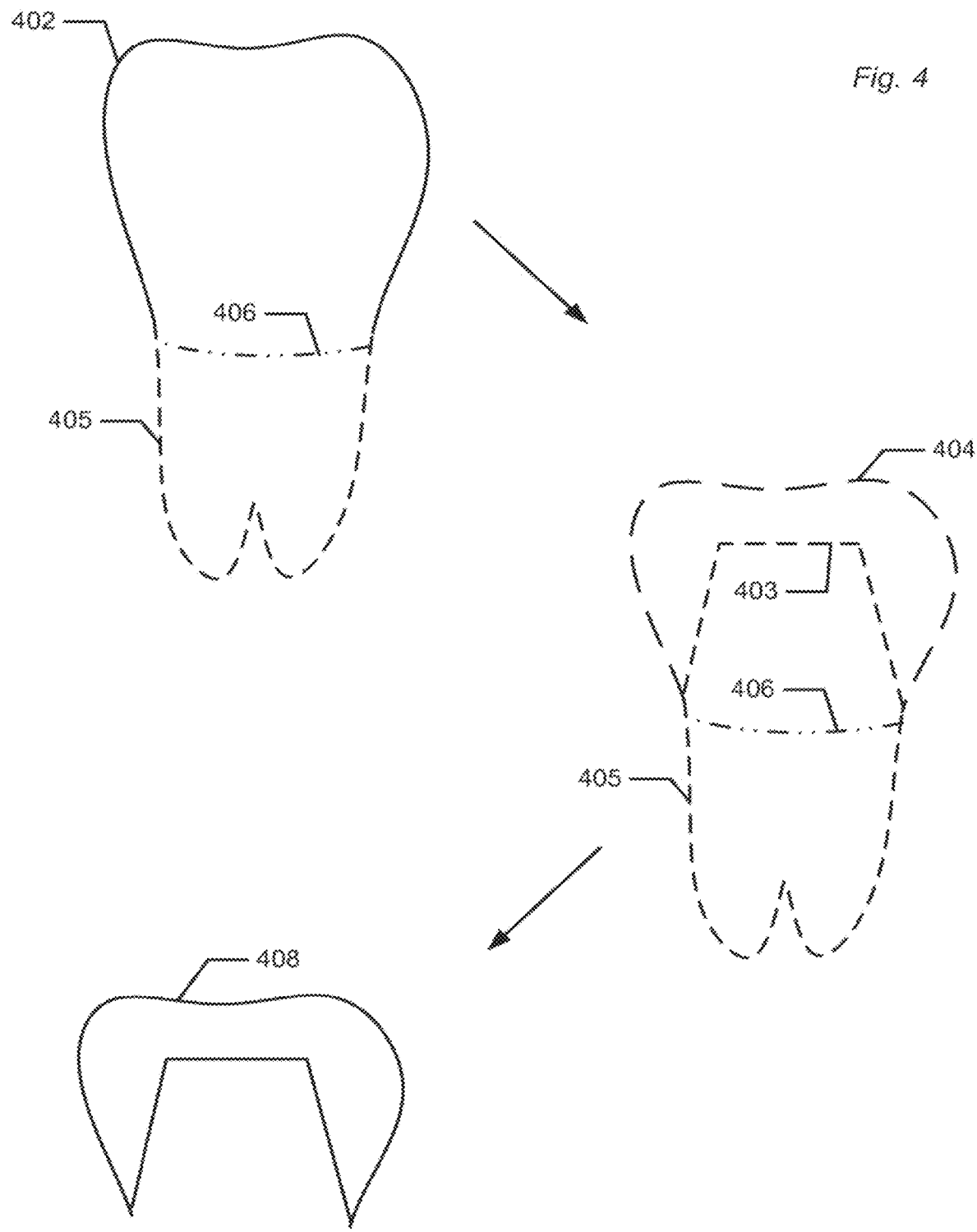
FIG. 4 shows an example of obtaining a virtual model of at least part of a dental component.

FIG. 4 shows an example of obtaining a virtual model of at least part of a dental component.

In the first figure, the tooth 402 is shown, the determined sub-gingival part 405 of the tooth 402 is shown, and the margin line 406 is shown. The sub-gingival part 405 of the tooth 402 and/or the margin line may be determined by the original shape of the tooth 402.

In the second figure, the virtual design of the crown 404 is shown, the virtual design of the preparation 403 is shown, the margin line 406 is shown and the sub-gingival part 405 of the tooth 402 is shown.

In the third figure, the final 3D virtual model 408 of the crown 404 is illustrated with a cross sectional of the virtual model.

Figure 5:
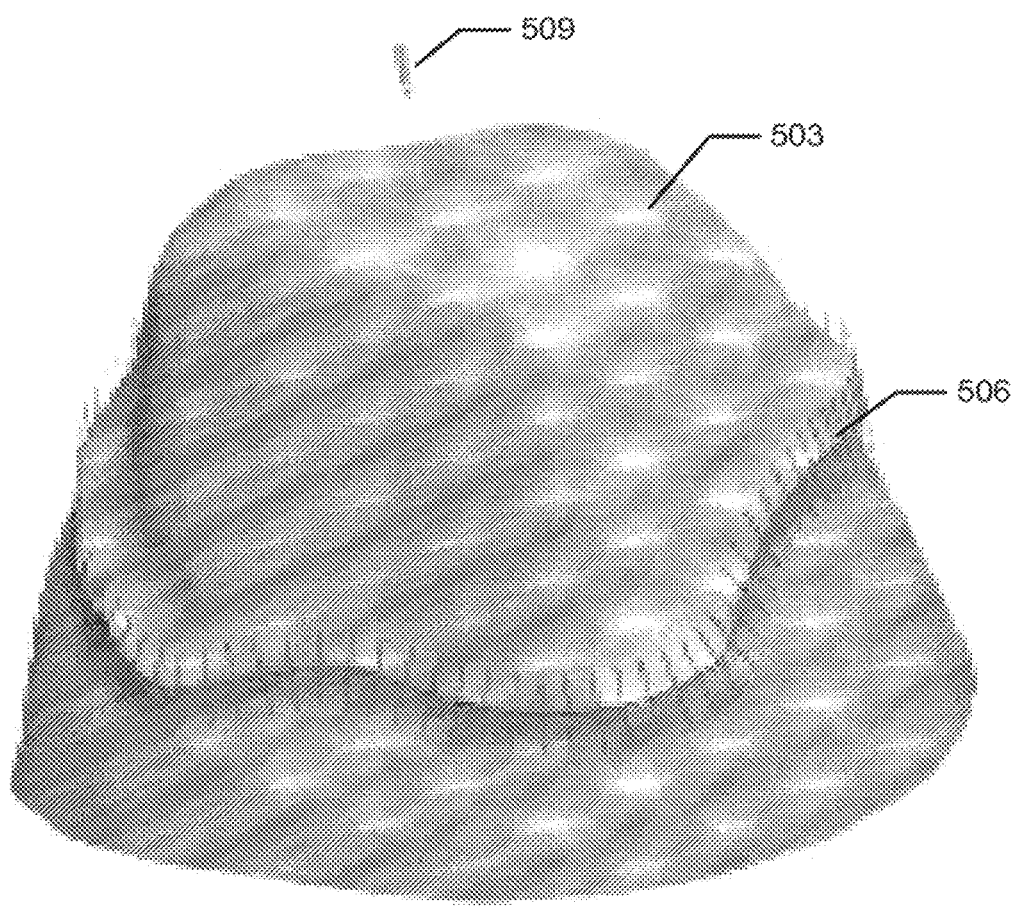
FIG. 5 shows an example of a margin line drawn on a preparation.

FIG. 5 shows an example of a margin line drawn on a preparation.

The margin line 506 is drawn on the preparation 503 and the insertion direction 509 of the preparation 503 is marked with an arrow.

Figure 6:
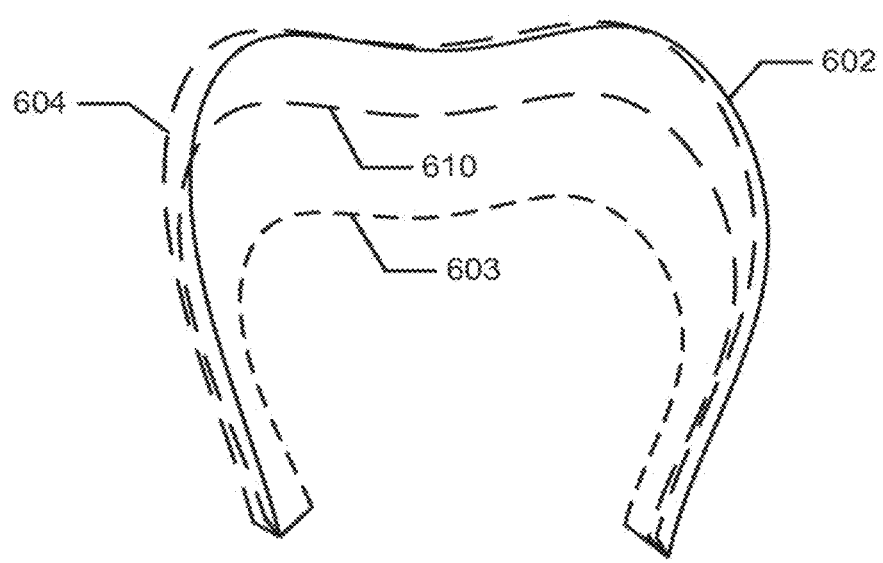
FIG. 6 shows an example of a crown designed based on the original tooth shape.

FIG. 6 shows an example of a crown designed based on the original tooth shape.

The original tooth shape 602 is a 3D representation from a 3D scan. The virtual design of the crown 604, which is a dental component or is a part of a dental component, is based on the original tooth shape 602 and/or based on the virtual preparation 603. The crown 604 may be the external part of a double crown, and the line 610 may then indicate the internal part 610 of the crown.

Alternatively, the line 610 may indicate a coping 610 for the crown 604 or a coping 610 for veneering 604.

There may be a cement space or gap between the two parts 604 and 610 for fastening them together.

Figure 7:
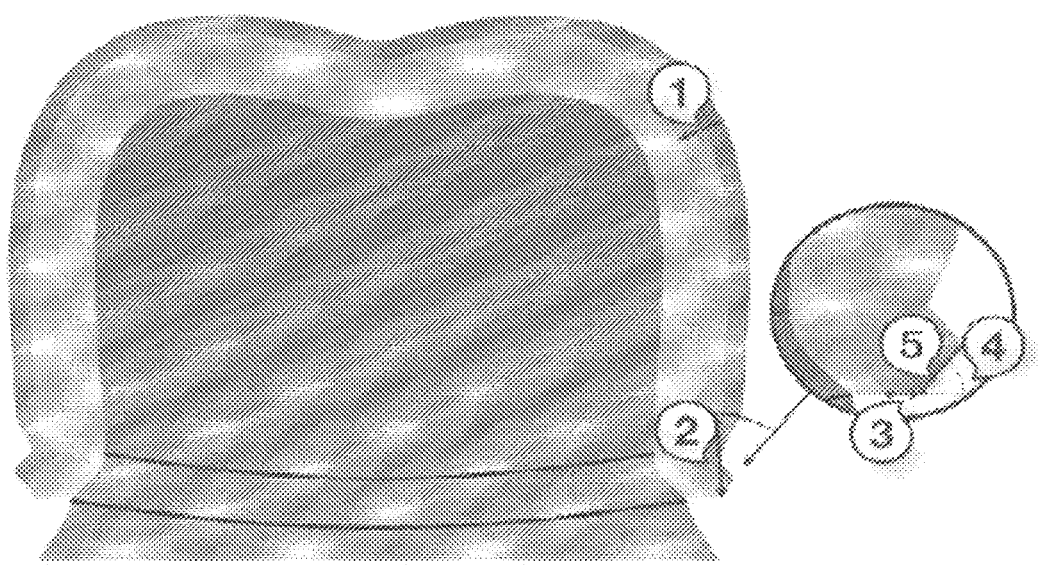
FIG. 7 shows a schematic example of choosing settings for a coping.

FIG. 7 shows a schematic example of choosing settings for a virtual preparation.

The virtual preparation may be designed based on a coping. Setting nr 1 indicates wall thickness of the coping, nr. 2 indicates wall height, nr. 3 indicates margin line offset, nr. 4 indicates offset angle, and nr. 5 indicates extension bandwidth. Lingual band start angle, end angle and offset can also be determined.

FIG. 8 shows examples of different dental components, where a preparation may be performed for attaching or arranging the dental component.

Figure 8A:
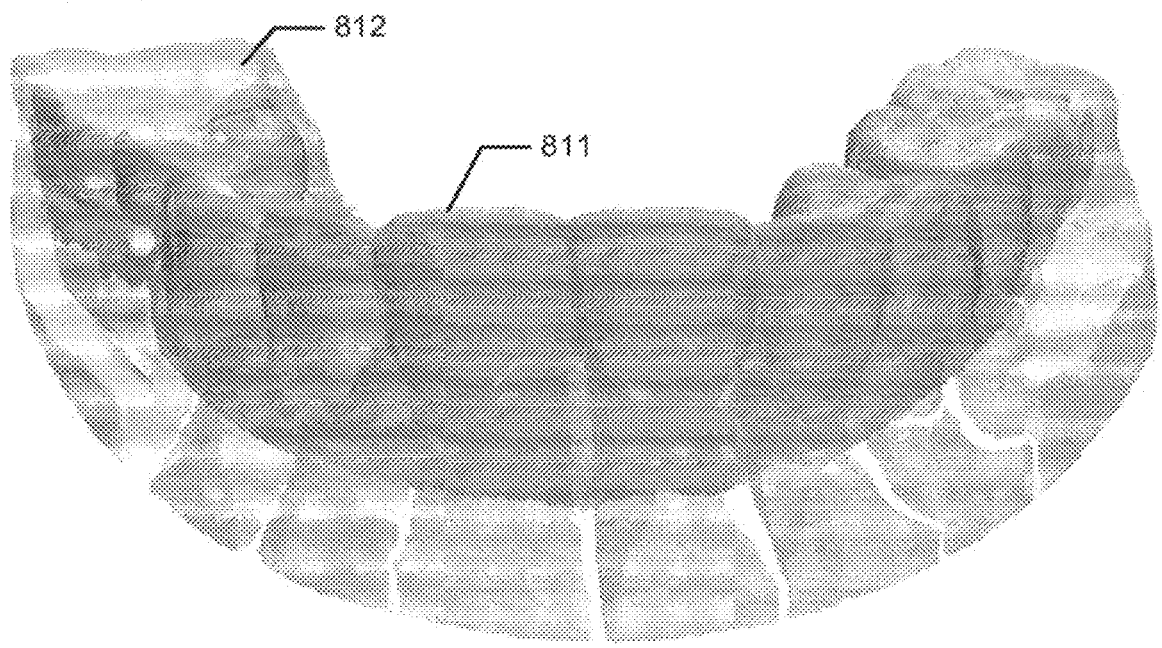
FIGS. 8a through 8d show examples of different dental components, where a preparation may be performed for attaching or arranging the dental component.

FIG. 8a) shows an example of a diagnostic wax-up 811 on a preparation or pre-preparation model 812. The diagnostic wax-up 811 and the model 812 may be virtual or physical.

Figure 8B:
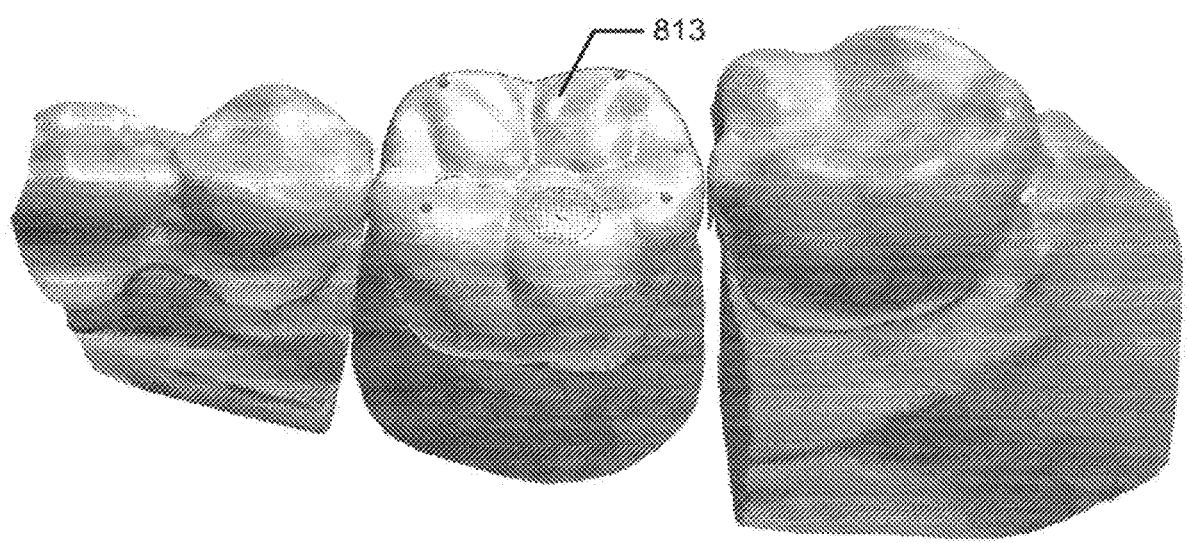

FIG. 8b) shows an example of crown 813 between the original neighboring teeth.

Figure 8C:
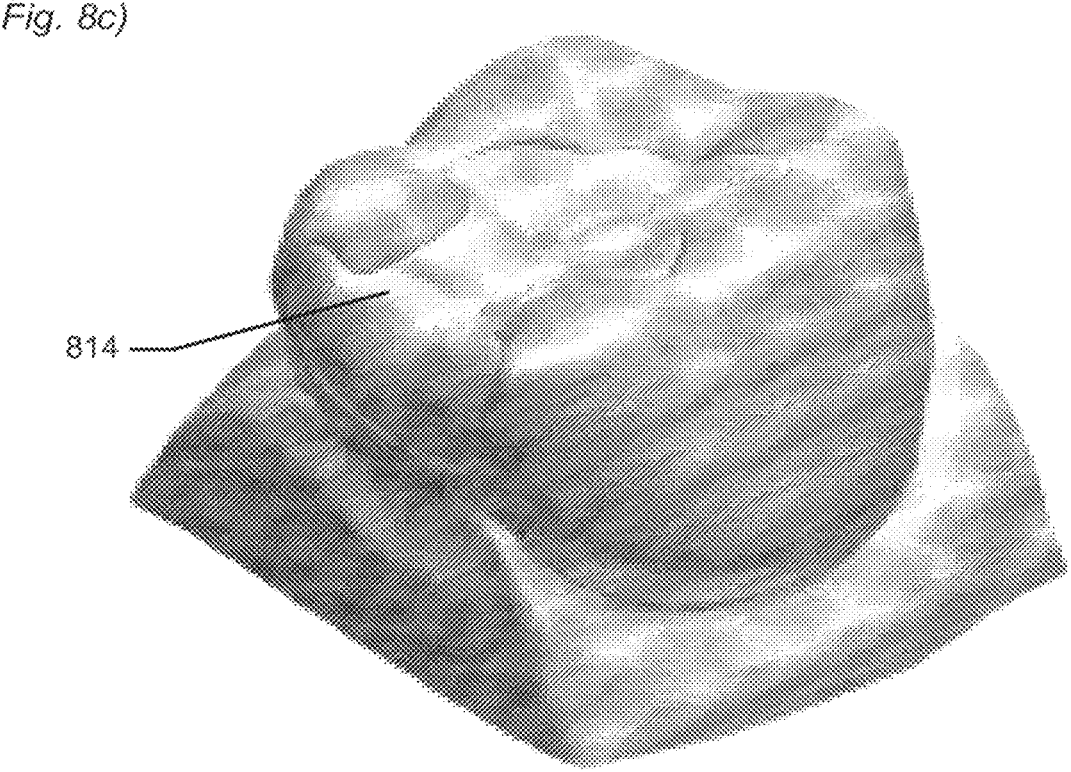

FIG. 8c) shows an example of inlay, onlay and veneers 814.

Figure 8D:
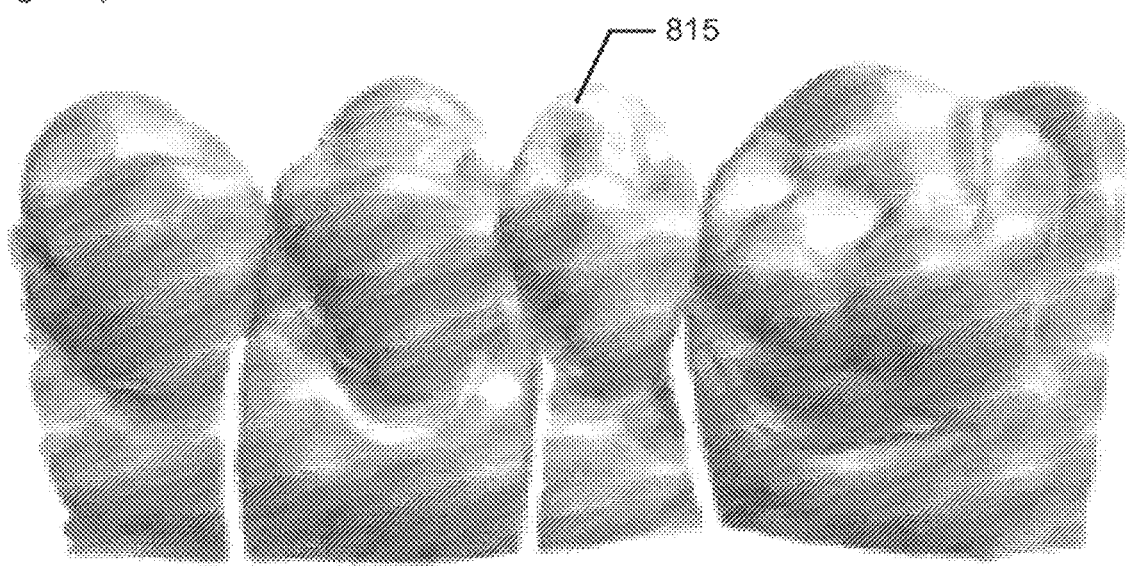

FIG. 8d) shows an example of inlay and Maryland bridge 815.

FIG. 9 shows an example of a workflow for designing a dental component, such as a temporary restoration, and a substantially corresponding dental component, such as a final restoration.

Figure 9A:
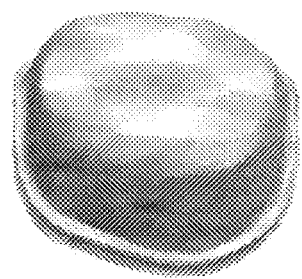
FIGS. 9a through 9h show an example of a workflow for designing a dental component, such as a temporary restoration, and a substantially corresponding dental component, such as a final restoration.

FIG. 9a) shows an example of a virtual preparation. The virtual preparation may be designed by e.g. a dental technician in a dental laboratory. The virtual preparation is designed based on a virtual 3D model of a patient's teeth. The virtual preparation may be a so-called minimal preparation. The virtual 3D model of the patient's teeth may be created based on e.g. an intra-oral scan, a scan of an impression, a scan of a model etc.

If the virtual 3D model is made based on an intra-oral scan or a scan of an impression, this removes the need for manufacturing a physical model of the teeth. The 3D scanning is performed on the pre-prepared set of teeth.

Figure 9B:
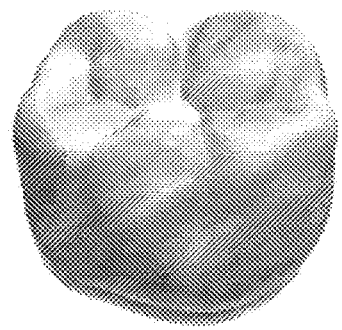

FIG. 9b) shows an example of a temporary restoration, which may be designed based on the virtual preparation in FIG. 9a). The dental technician may also design the temporary or a diagnostic wax-up. The internal surface of the temporary may automatically be processed or designed to fit the virtual preparation.

Figure 9C:
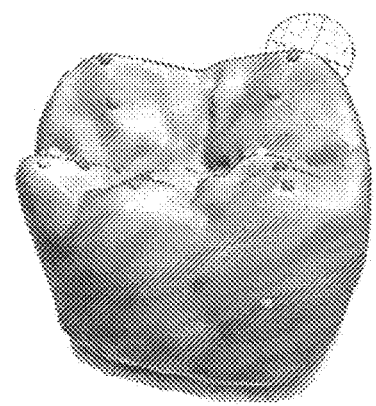

FIG. 9c) shown an example where the design of the temporary in FIG. 9b) may be performed by means of CAD design and using e.g. tooth libraries, cloning with existing teeth and/or freeform modeling using flexible sculpt tools. The sculpt tools may provide scaling, shaping, rotating, cloning, mirroring, morphing etc.

The digital design of the temporary or diagnostic wax-ups can be sent digitally to the laboratory manufacturing them. Furthermore, the dental technician can send accurate before-and-after visualizations of the designed tooth and resulting smile for reviewing at the dentist clinic.

At the manufacturer, the temporary or diagnostic wax-up can be manufactured directly from the CAD design and sent to the dentist. When the dentist receives the temporary, he then actually prepares, grind, or preps the patient's real tooth. Then he takes an impression of the new dental situation with the prepared tooth using impression material and/or scans the teeth intra orally, and then he places or seats the temporary restoration in the patient's mouth. The impression and/or the intra oral scan may be sent to the dental technician or laboratory that scans the impression to obtain a virtual 3D model of the preparation or obtains or uses the 3D model created from the intra oral scan.

Figure 9D:
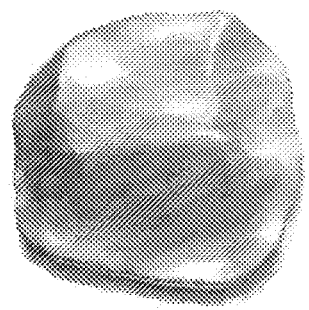

FIG. 9d) shows an example of a virtual 3D model of the real preparation.

Figure 9E:
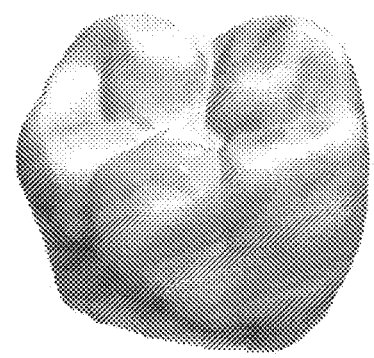

FIG. 9e) shows an example of the designed final restoration. The virtual 3D model of the preparation and the previously made digital temporary design may be used to create the design of the final restoration, e.g. a crown. This design may also be performed by the dental technician and/or the laboratory. The temporary restoration design files may be merged together with the virtual 3D model of the preparation to create a final crown using digital transfer and align processing tools or means. The final crown may thus be created in a very short time and with a perfect fit to the patient's tooth preparation.

Figure 9F:
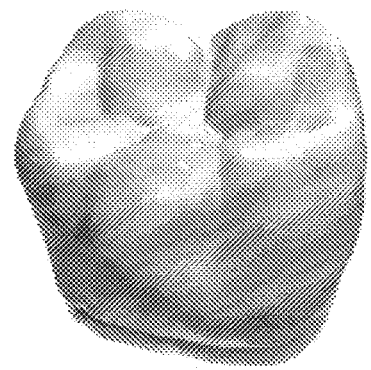

FIG. 9f) shows an example of the final restoration arranged on the preparation.

Figure 9G:
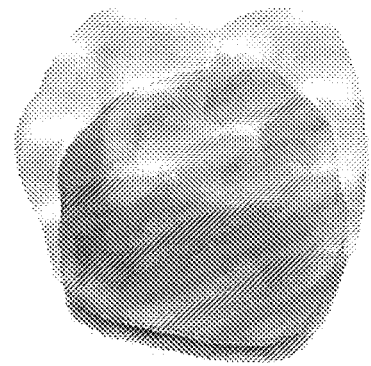

FIG. 9g) shows an example of the final restoration arranged on the preparation where the final restoration is transparent such that the preparation can be seen underneath.

Figure 9H:
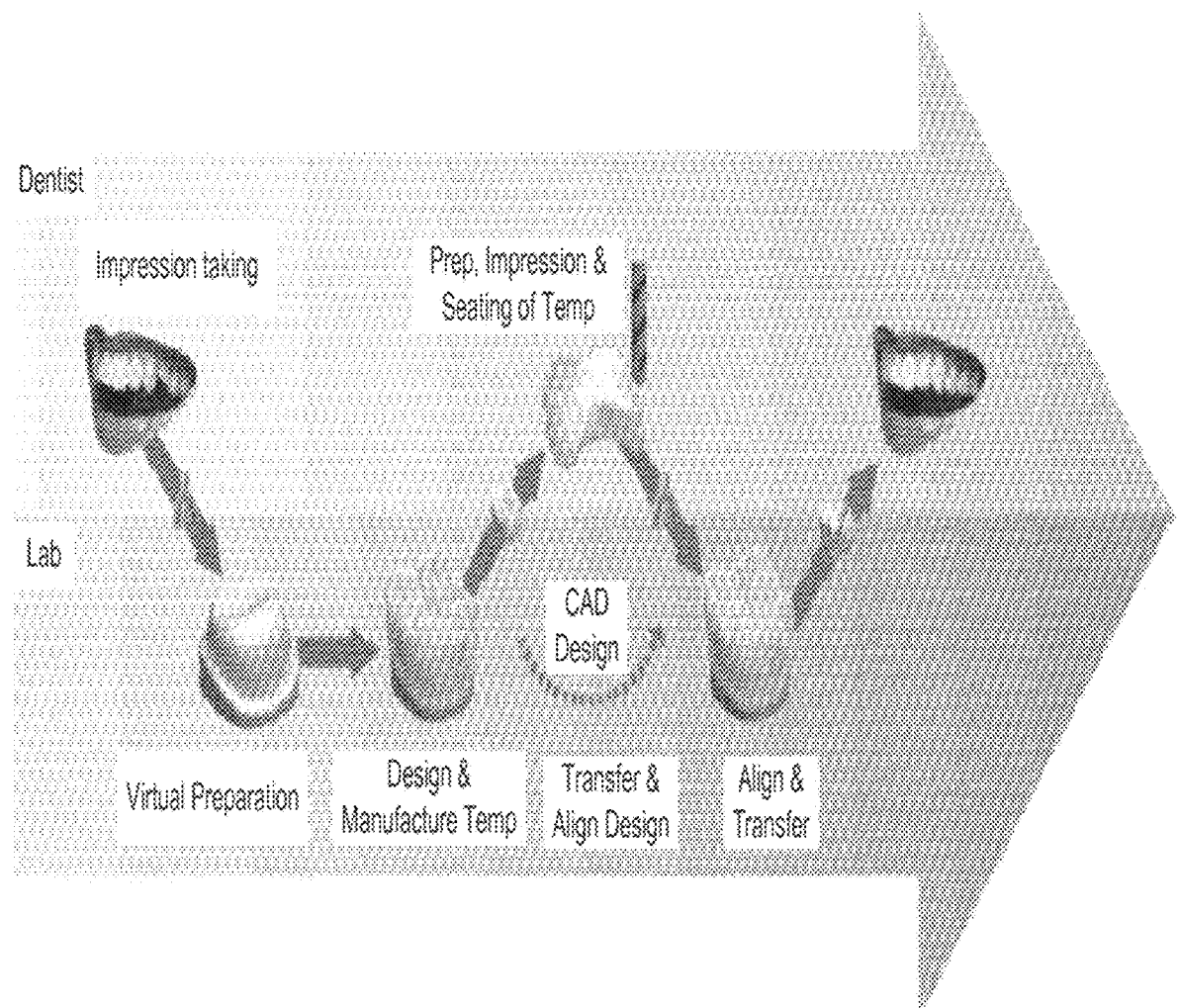

FIG. 9h) shows an overview of one workflow illustrated with the figures above. The temporary restoration is denoted as "temp" in this figure. The figure illustrates how the actions are divided between the dentist and laboratory or lab.

FIG. 10 shows an example of designing at least a part of a dental component based on a gingival part.

Figure 10A:
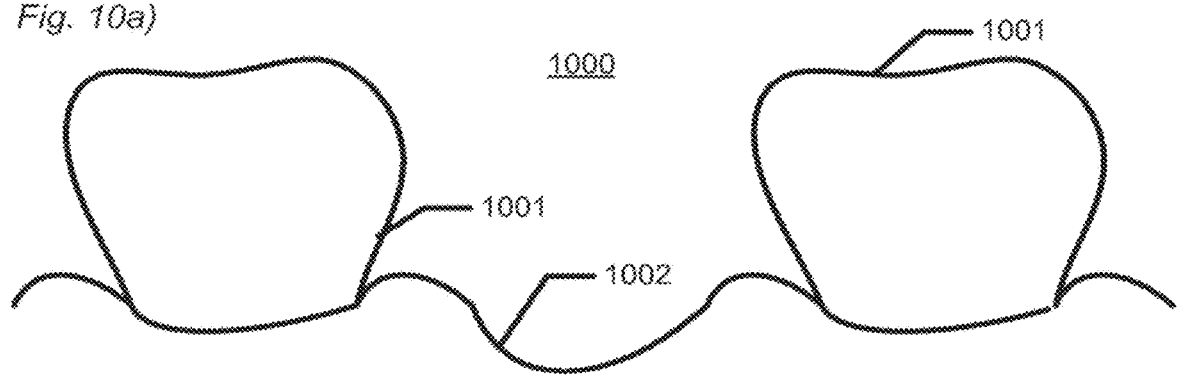

FIG. 10a) shows an example of a 3D virtual model 1000 of a patient's teeth. The 3D virtual model 1000 may be obtained by scanning the teeth with an intra oral scanner, scanning an impression of the teeth or scanning a physical model of the teeth. The virtual model 1000 comprises in this case two teeth 1001 and the gingival edge 1002 of a region which may be an extraction wound after a tooth being removed or falling out or dying. Thus the patient wishes to have a bridge made where a pontic is arranged in the place 1002 of the missing tooth.

Figure 10B:
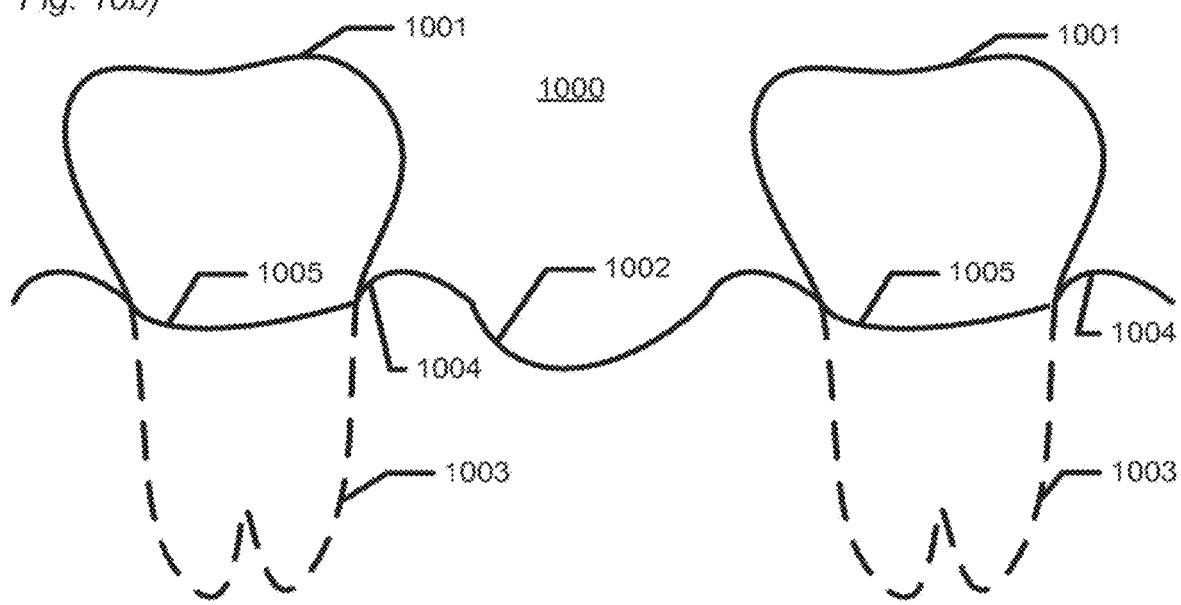

FIG. 10b) shows an example of the 3D virtual model 1000 where the tooth roots 1003 in the bone hidden by the gingival 1004 is indicated. The line 1005 on the teeth 1001 indicates where the gingival reaches on the teeth 1001.

Figure 10C:
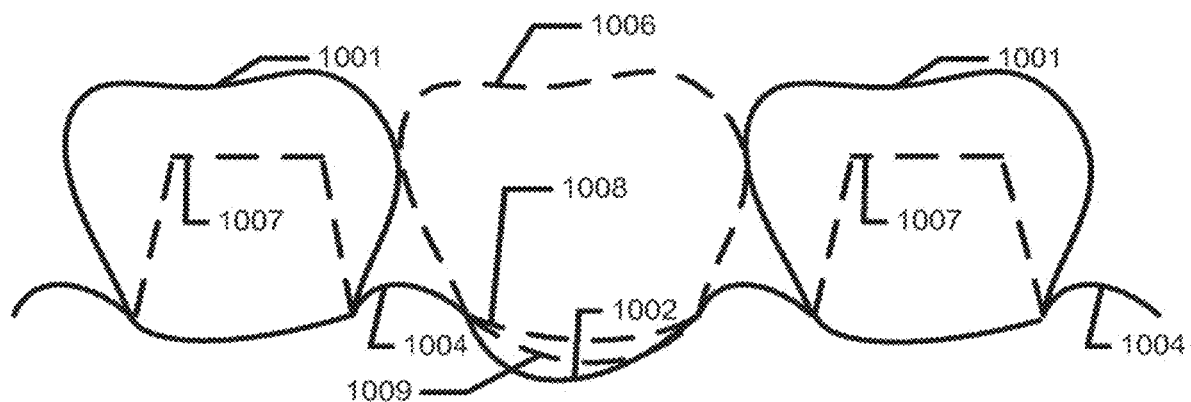

FIG. 10c) shows an example of the designed temporary restoration 1010, which is a bridge in this example. The designed pontic 1006 is indicated between the two teeth 1001. The preparation 1007 of each of the two teeth 1001 is also indicated. Furthermore, the edge of the pontic adjacent to the gingival edge 1002 of the extraction region is shown in two different designs 1008 and 1009. The edge of the pontic 1008, 1009 is designed relative to the gingival edge 1002 of the extraction region.

The pontic edge 1008 provides a shorter pontic, where in this case the gap between the pontic edge 1008 and the gingival 1002 of the broken region will be rather big. The pontic edge 1009 provides a longer pontic, where in this case the gap between the pontic edge 1009 and the gingival 1002 of the broken region will be smaller. The pontic edge 1009 may correspond to the pontic edge in a temporary restoration, where the region after the missing tooth is rather big. The pontic edge 1008 may correspond to the pontic edge in a final restoration, where the region after the missing tooth is smaller since the bone underneath may have grown and the gingival edge 1002 is in good shape again. The patient normally wears the temporary restoration for some weeks and in this period the bone may start growing and the extraction wound may heal. Thus the final restoration should typically be smaller than the temporary for ensuring that the gap to the gingival edge 1002 is still suitable.

Notice that the gaps between the pontic edge 1008, 1009 and the gingival edge 1002 shown in this figure are exaggerated for the purpose of illustration. Normally the gap should be so small that it is not immediately visible and so food stuff etc. does not come in through the gap. Still the gap should have a size so that the edge of the pontic 1008, 1009 does not irritate the adjacent gingival edge 1002.

Figure 10D:
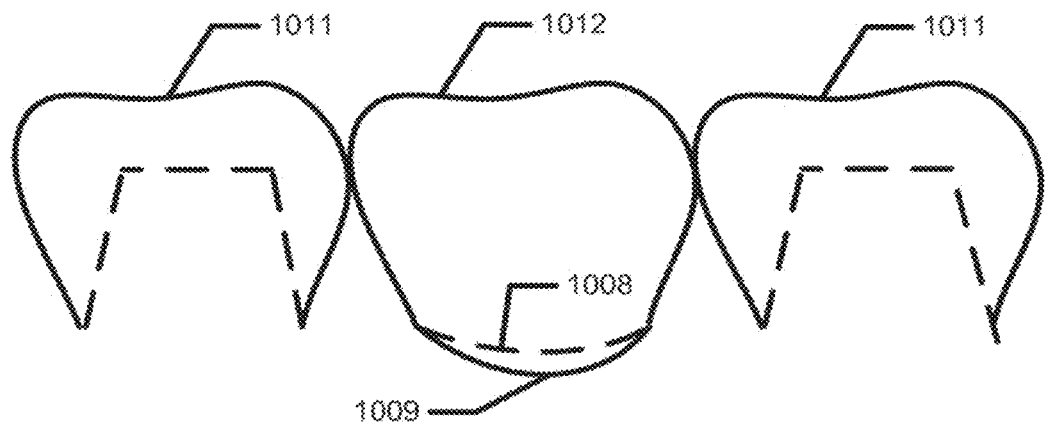

FIG. 10*d*) shows an example of the temporary restoration 1010 comprising two crowns 1011 and a pontic 1012. The edge 1009 indicates the edge of the temporary restoration. The dotted line 1008 may indicate the edge of a final restoration.

The internal part of the crowns 1011 of the restoration 1010 corresponds to the preparation 1007 as seen in FIG. 10*c*).

Figure 10E:
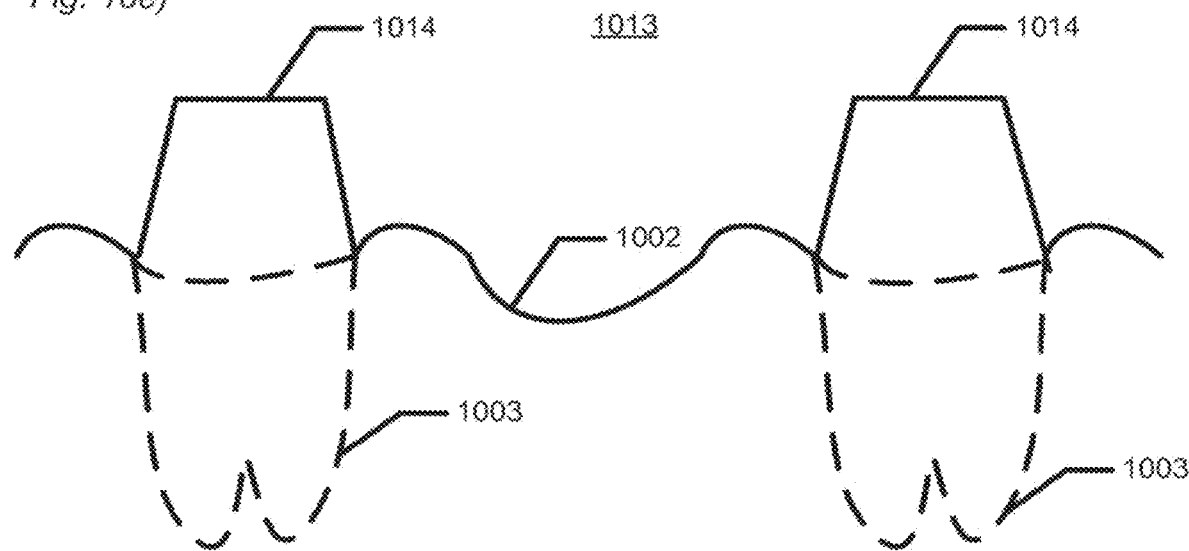

FIG. 10*e*) shows an example of a 3D virtual model 1013 of the teeth after the dentist has prepared the two teeth for the crowns. The teeth 1001 from FIG. 10*a*) are now prepared teeth 1014. The prepared teeth 1014 correspond to the designed preparation 1007 in FIG. 10*c*). The tooth roots 1003 are also shown.

Figure 10F:
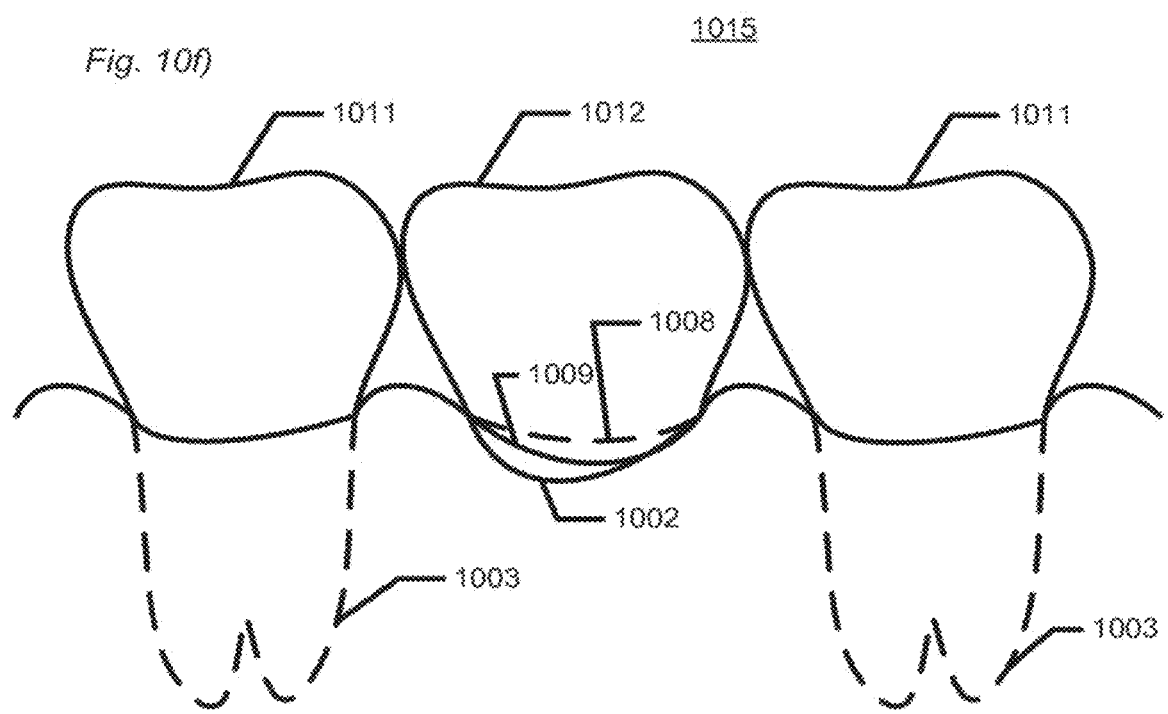

FIG. 10*f*) shows an example of the oral situation 1015 when the restoration is arranged in the mouth of the patient. The restoration comprises the two crowns 1011 and the pontic 1012. The tooth roots 1003 are also indicated for illustration. The pontic edge 1009 of the temporary restoration is shown, as well the pontic edge 1008 for e.g. a final restoration. The edge of the gingival 1002 in the wound or hole is indicated.

FIG. 10*g*) shows an example of the oral situation 1015 when the temporary restoration is arranged in the mouth of the patient. The restoration comprises the two crowns 1011 and the pontic 1012. The pontic edge 1009 of the temporary restoration is shown.

FIG. 10*h*) shows an example of the oral situation 1015 when the final restoration is arranged in the mouth of the patient. The restoration comprises the two crowns 1011 and the pontic 1012. The pontic edge 1008 of the final restoration is shown.

FIG. 11 shows examples of designing of the gingival.

Figure 11A:
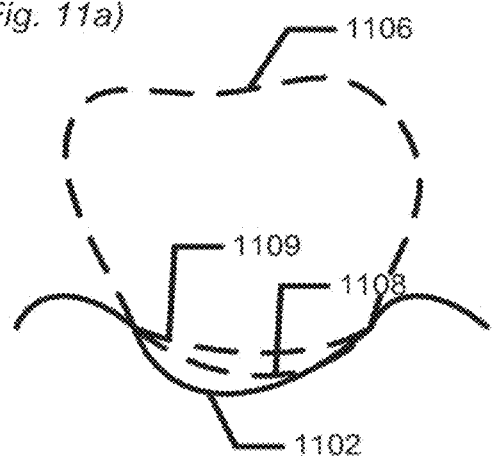
FIGS. 11a through 11e show examples of designing of the gingival.

FIG. 11*a*) shows an example of a pontic 1106 and the gingival edge 1102 adjacent to the pontic. The dotted lines 1108 and 1109 show how the edge of the pontic adjacent to the gingival edge 1102 can be designed.

Figure 11B:
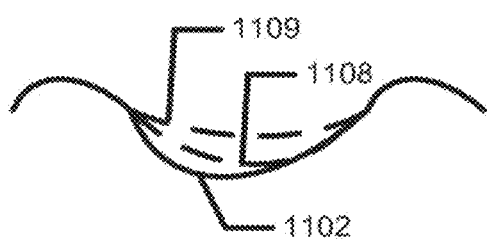

FIG. 11*b*) shows an example of the gingival edge 1102 and two designs of a pontic edge 1108, 1109, which are designed based on the gingival edge 1102.

Figure 11C:
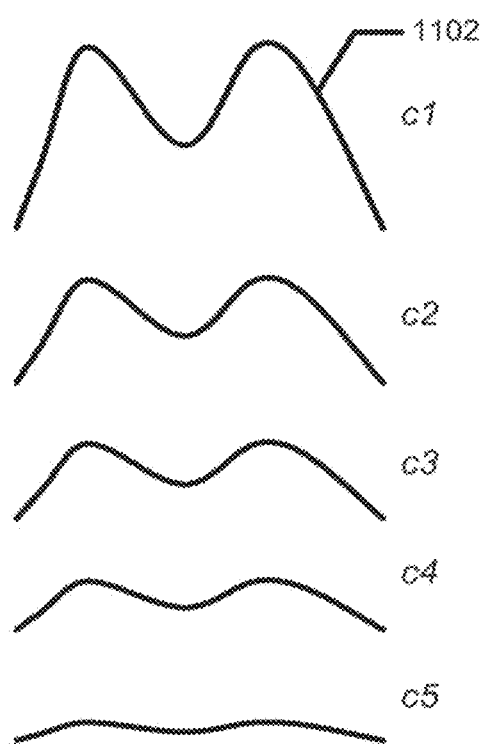

FIG. 11*c*) shows an example of designing the gingival edge 1102. The gingival edge c1 may be gingival edge as captured in the mouth of the patient. The gingival edge may be scanned intra orally or an impression of the teeth and gingival may be taken.

The designs c2-c5 may be different designs of the gingival edge 1102. The gingival edge may be designed like this, because the dental technician and/or the dentist assume that the gingival edge will evolve to look like this after some time. Based on the design of the gingival edge 1102, a restoration, such as a temporary restoration, such as a pontic in a bridge, may be designed.

Figure 11D:
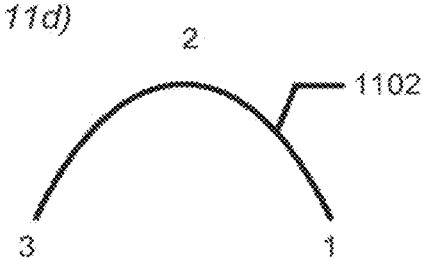
Figure 11E:
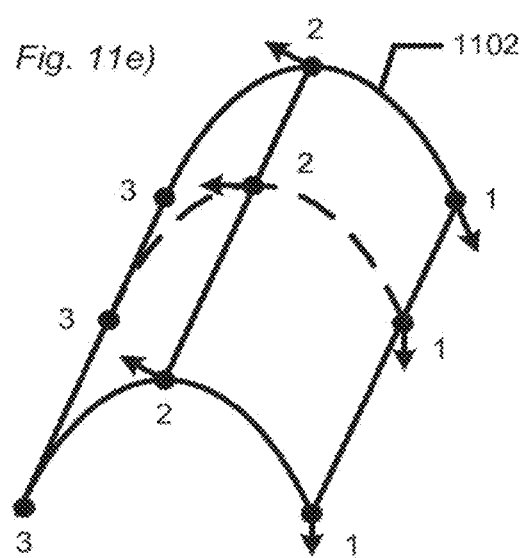

FIG. 11*d*) and FIG. 11*e*) show an example of modeling or designing or sculpting the gingival edge 1102. A number of points, e.g. three points, 1, 2, 3, may be assigned to the gingival edge for dragging the edge in different directions, depending on how the design of the gingival should be. As it is shown in the figure, the points along the gingival edge may be dragged in different directions for designing the gingival.

In some of the FIGS. 2D models are shown and the designing or modeling is shown in 2D, however it is understood that all models according to the method are 3D models and that designing and modeling are in 3D in the method.

FIG. 12 shows an example of prior art manual designing of the gingival on a physical teeth model.

Figure 12A:
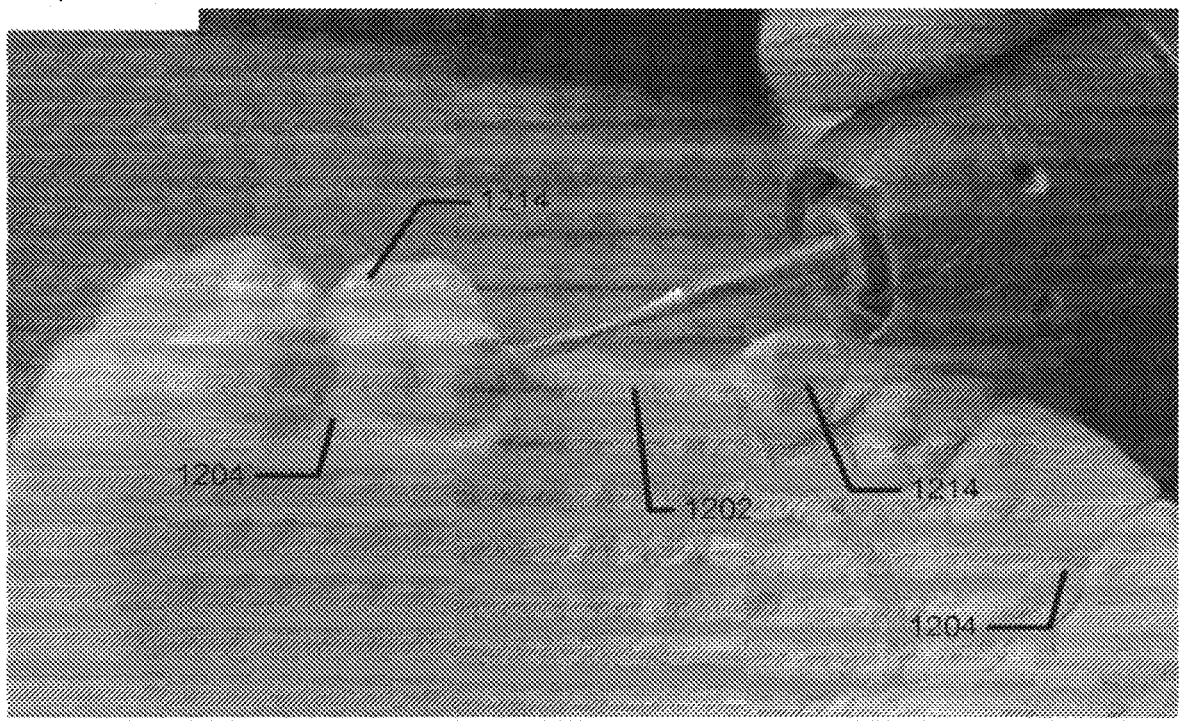
FIGS. 12a through 12c show an example of prior art manual designing of the gingival on a physical teeth model.

FIG. 12*a*) shows the manual preparation of the prepared teeth 1214 on the physical model with a grinding tool. The region 1202 shows the gingival edge where one or more teeth are missing. The regular gingival 1204 is seen around the normal teeth.

Figure 12B:
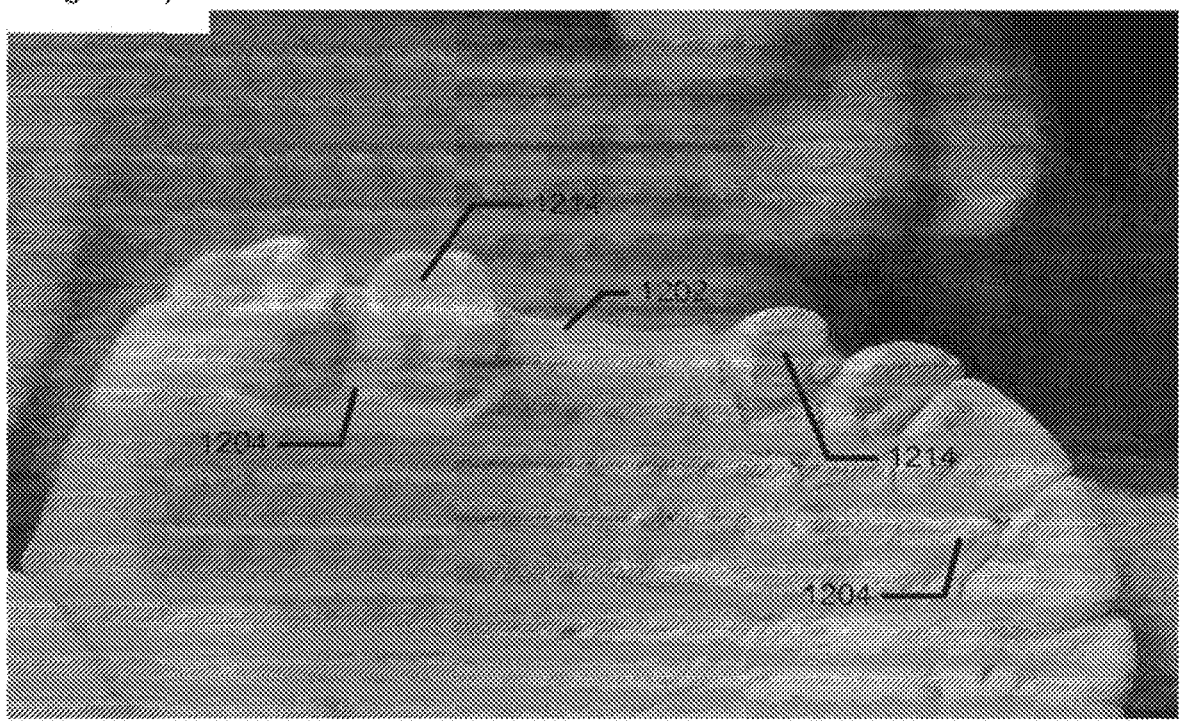
Figure 12C:
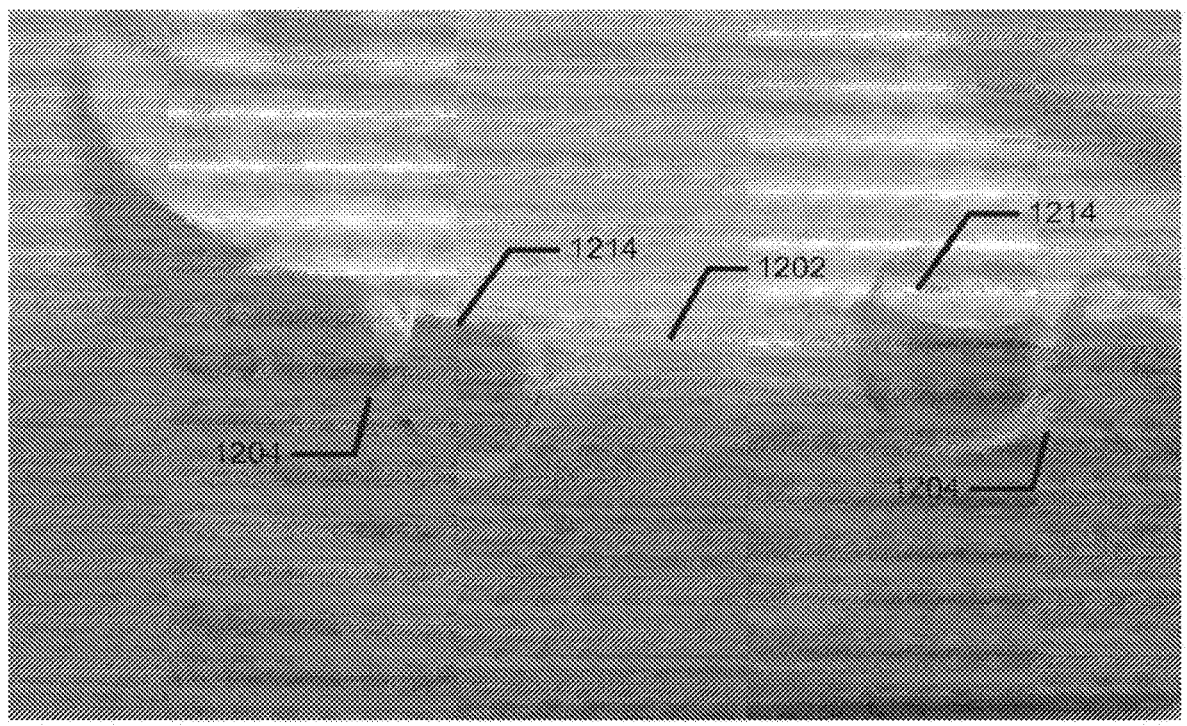

FIG. 12*b*) and FIG. 12*c*) shows same physical model with the prepared teeth 1214. The region 1202 shows the gingival edge where one or more teeth are missing. The regular gingival 1204 is seen around the normal teeth.

A bridge with a pontic arranged at the region with the gingival edge 1202 can then manually be designed for this model.

FIG. 13 shows an example of how a 3D virtual model of a temporary bridge restoration for the patient's set of teeth can be generated using an embodiment of the invention.

The illustrated temporary bridge restoration is for the anterior maxillary teeth, such that pontics are provided for the 8-tooth and the 9-tooth, while crowns of the bridge are attached to the 7-tooth and the 10-tooth, where the teeth are numbered according to the universal tooth designation system. The reference numbers used in the figure complies with this numbering such that e.g. reference numbers 1307 and 1310 are used for the teeth that in the universal tooth designation system are numbered 7 and 10, respectively.

Figure 13A:
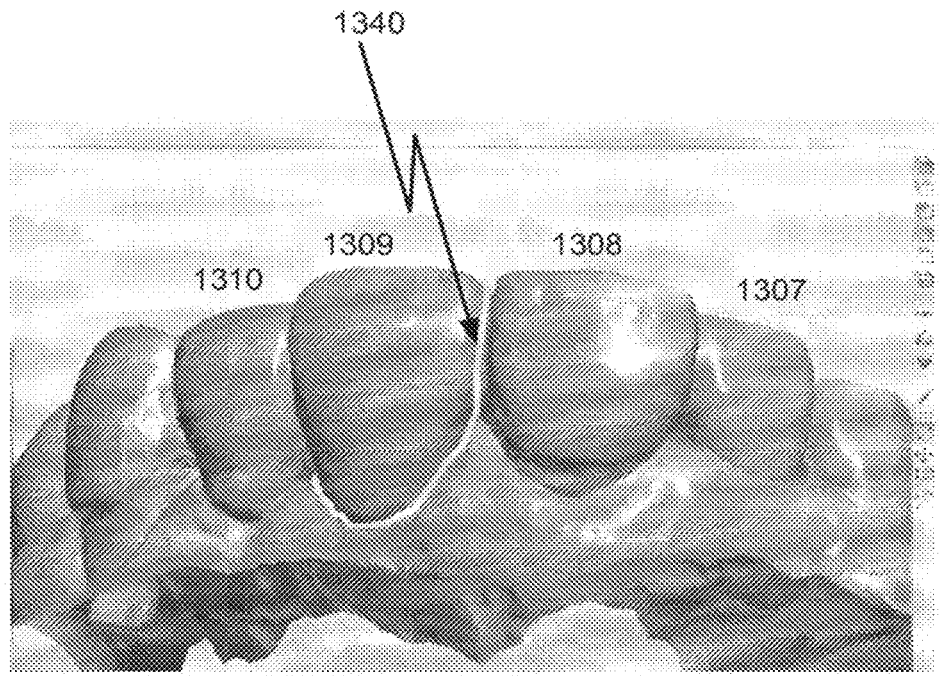
FIGS. 13a through 13i show an example of the generation of a virtual model of a temporary bridge restoration.

FIG. 13*a*) shows a digital 3D representation of the pre-prepared set of teeth where a 3D sectioning spline 1340 has been defined on the 9-tooth. The 3D sectioning spline can be defined manually by an operator or automatically using computer implemented algorithms. The digital 3D representation is generated from a 3D scan of the pre-prepared set of teeth.

After the 3D sectioning spline has been defined in relation to one tooth, the inter-proximal surfaces and optionally some of the sub-gingival surface of this tooth can be generated using computer implemented algorithms.

The 3D sectioning spline can be modified to provide that it has the same relationship to the gingival over the inter-proximal surfaces and the buccal/labial/lingual facing surfaces of the tooth. That is, the 3D sectioning spline 1340 can be modified to have a desired shape over the inter-proximal surfaces and over the directly visible surfaces of the tooth.

In FIG. 13*a*) the 3D sectioning spline 1340 follows the gingival on the labial-facing surface of the 9-tooth 1309. The 3D sectioning spline can be defined by control points which accordingly can be used to modify the 3D sectioning spline to substantially follow the gingival over the buccal or lingual surfaces of the tooth as well as the inter-proximal surfaces of the tooth. When the 3D sectioning spline 1340 has been modified to have a desired shape, the part bounded by the 3D sectioning spline is virtually removed from the digital 3D representation.

The procedure of defining the 3D spline from the digital 3D representation of the pre-prepared tooth and modifying it to follow a desired path also in the inter-proximal surface of the tooth can be repeated for all teeth such that the portion of the digital 3D representation corresponding to all these teeth is deleted. This corresponds to virtually removing the teeth from the digital 3D representation of the set of teeth.

When the teeth are virtually removed from the set of teeth, the operator may choose to place a virtual gingival or a virtual preparation at the corresponding locations depending on whether the tooth is to be removed from the set of teeth or is to be prepared for a crown.

Figure 13B:
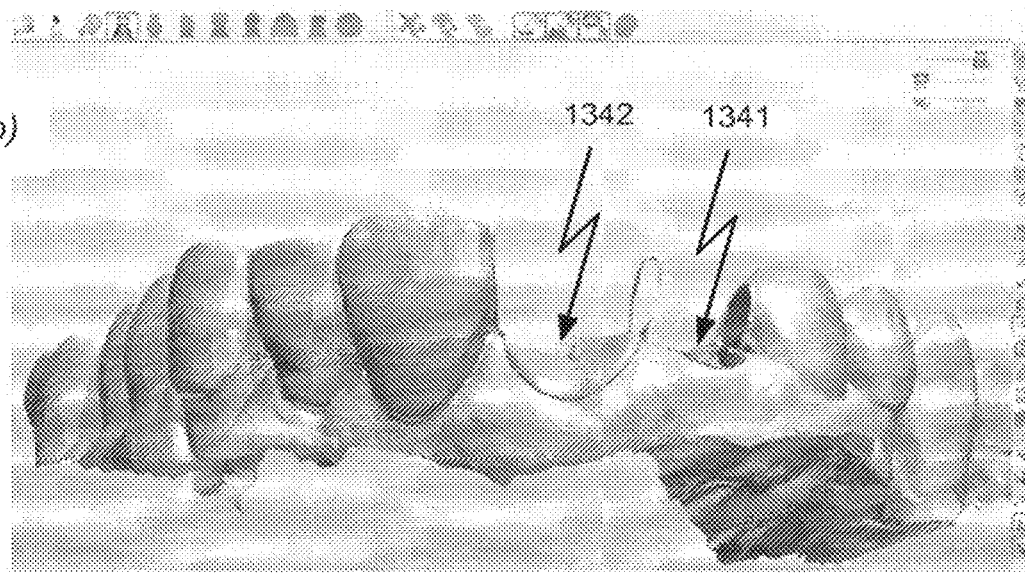

FIG. 13b) shows the digital 3D representation of the pre-prepared set of teeth after the 7-tooth and the 8-tooth are virtually removed. A hole 1341 is now seen in the region from which the 7-tooth has been removed, while a virtual gingival 1342 has been generated for the region from which the 8-tooth has been removed. The virtual gingival 1342 can be generated from a library and/or derived from the shape of the surrounding gingival using e.g. algorithms similar to a curvature based hole closing technique. The virtual gingival may also be shaped using points as described in FIG. 11e) where the points can be used to adapt first version of the gingival to the gingival of the patient. The first version of the gingival may be selected from a library or generated using an algorithm.

Figure 13C:
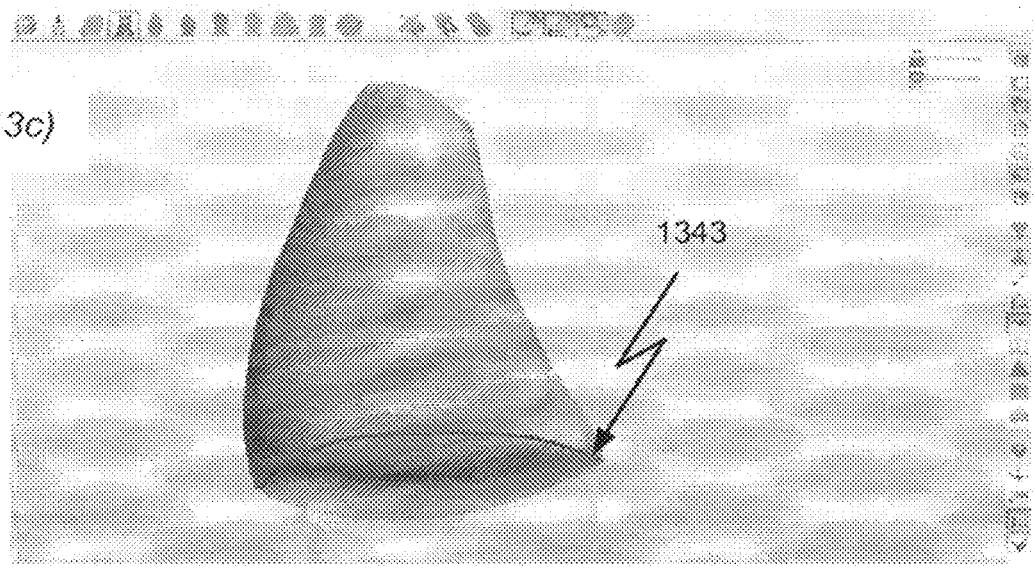

A virtual margin line of the individual teeth in the temporary bridge restoration may be defined. The virtual margin line can be configured to extend over the inter-proximal surfaces as seen in FIG. 13c) which shows a virtual margin line 1343 for the 7-tooth. The operator may choose to modify the margin line to achieve a desired aesthetic result.

Figure 13D:
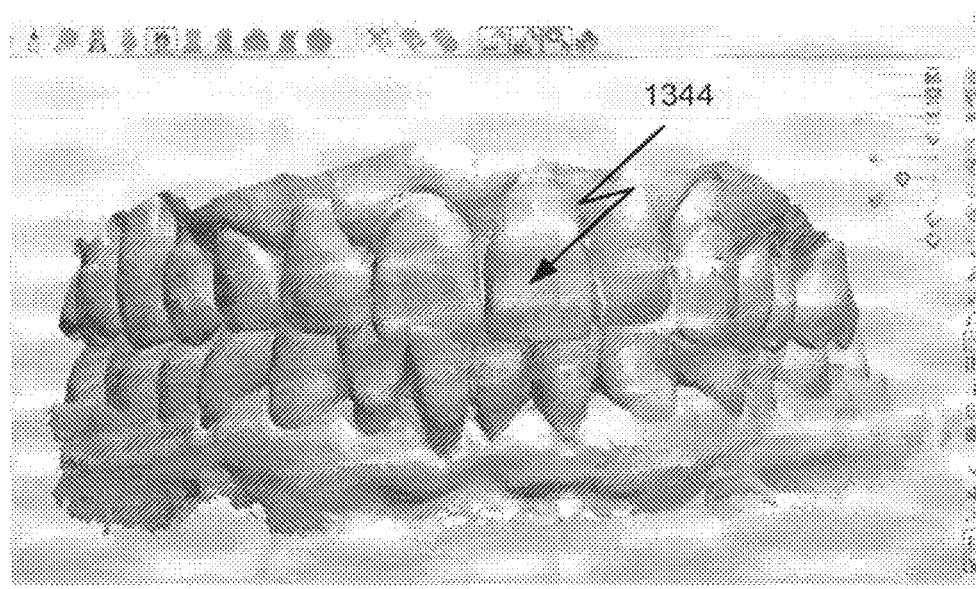

In FIG. 13d) a diagnostic bridge wax-up 1344 for the four teeth is provided and combined with the digital 3D representation of the set of teeth from which teeth are virtually removed to get a virtual model of a target dental situation. The diagnostic bridge wax-up 1344 can be selected from a library or be formed according to the teeth of the pre-prepared set of teeth. The anatomical surface of the teeth of the temporary bridge restoration can be derived from the teeth of the diagnostic bridge wax-up.

Figure 13E:
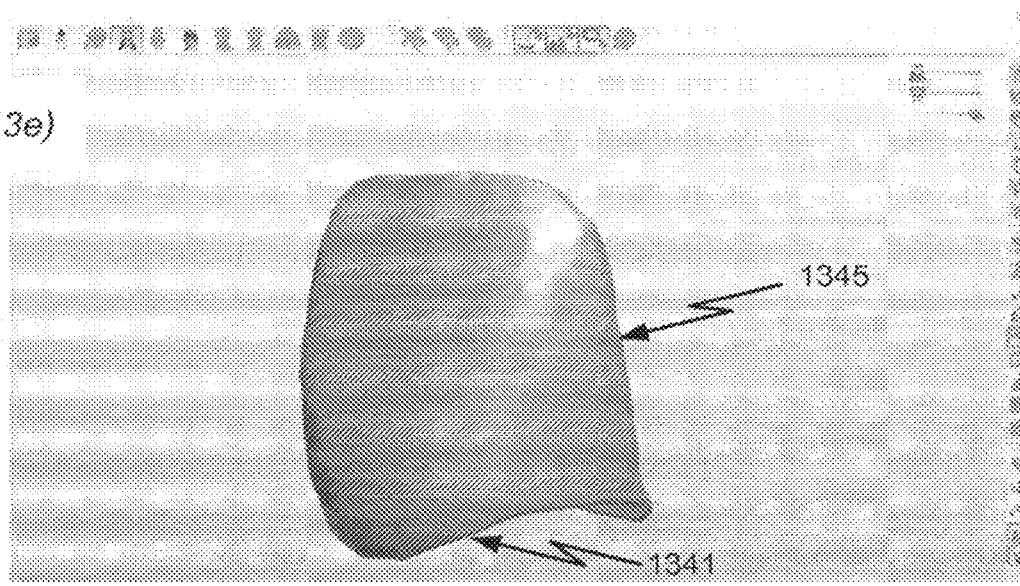

FIG. 13e) shows a virtual model of the crown part 1345 of the temporary bridge restoration where the boundary of the cervical edge of the crown is defined from the virtual gingival line 1341. The virtual margin line defined on the tooth seen in FIG. 13c) can hence be used to define the cervical edge (i.e. the lower boundary) of the corresponding part (crown or pontic) of the virtual model of the temporary bridge restoration FIG. 13f) shows a visualization of a virtual combined model of the digital 3D representation virtual of the teeth from which teeth are virtually removed and the diagnostic wax-up. The combined model may also be referred to as a virtual diagnostic lab model and it can show a target dental situation for the patient.

Holes that appears e.g. at the location where the diagnostic wax-up and the digital 3D representation connects may be closed using e.g. curvature based hole-closure algorithms such that the virtual diagnostic lab model is made "watertight".

Figure 13F:
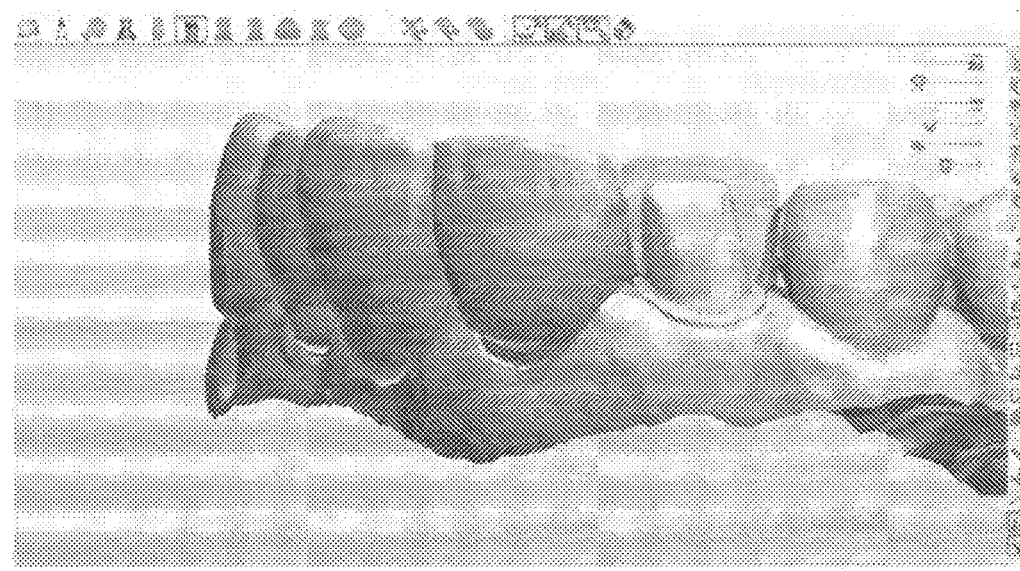

FIG. 13f) also shows a virtual preparation which has been added at the part of the digital 3D representation where the 7-tooth has been virtually removed. This can be advantageous in case the dental technician chooses to design the digital temporary restoration from the shape of the virtual preparation.

Figure 13G:
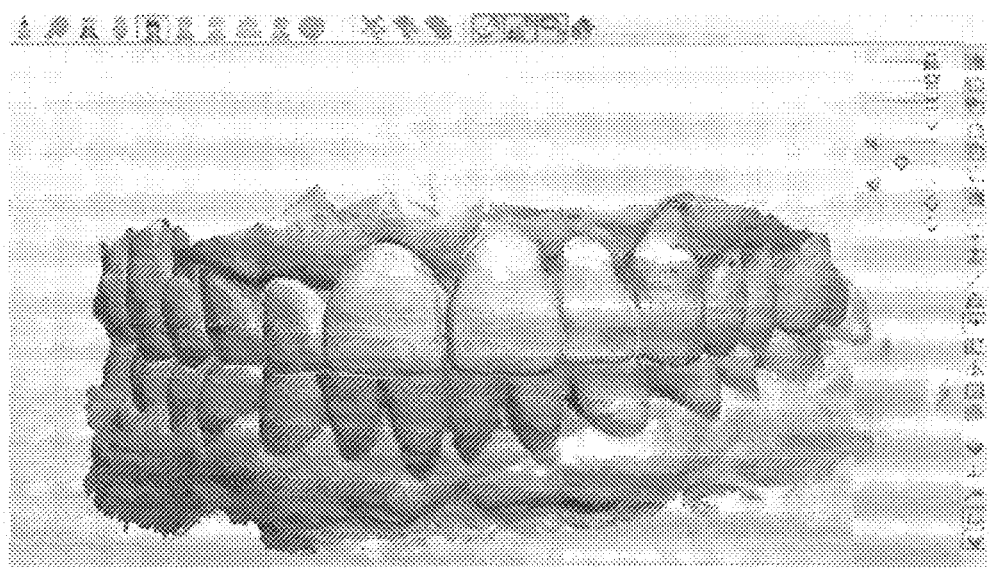

The diagnostic wax-up part of the virtual combined model can be manipulated independently of the digital 3D model of the set of teeth in order to obtain e.g. a desired aesthetic appearance as illustrated in FIG. 13g).

Figure 13H:
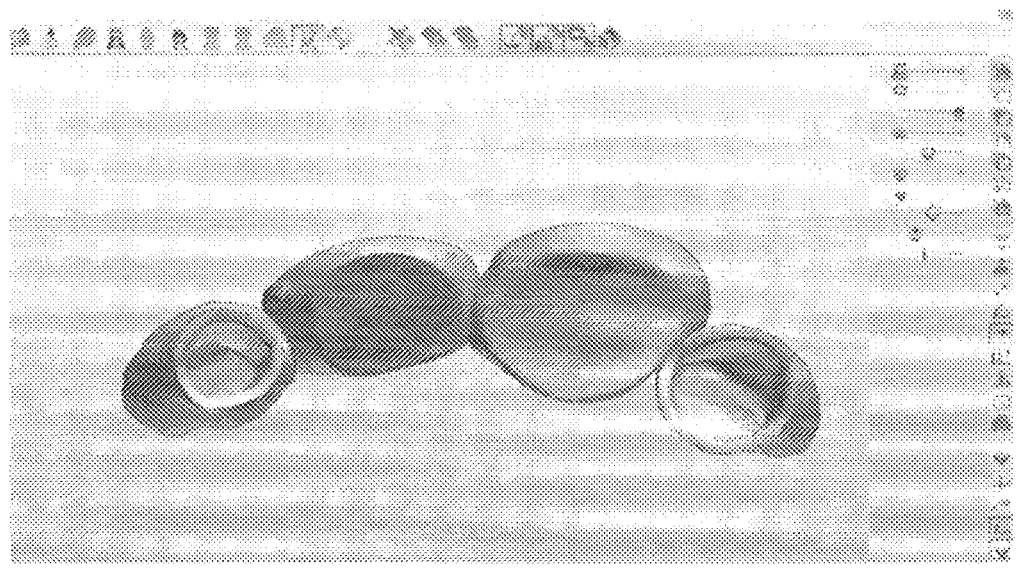
Figure 13I:
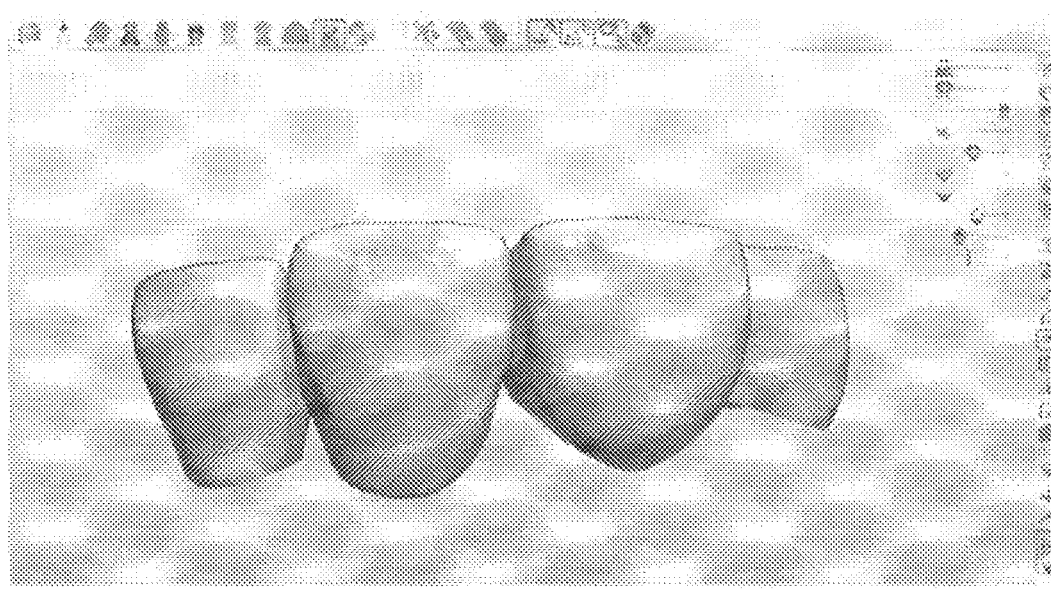

FIGS. 13h) and 13i) show the 3D virtual model of the temporary bridge restoration. In FIG. 13h) the temporary bridge restoration is viewed from the basal/cervical side such that the generated jaw-facing surfaces of the crowns and the pontics are seen. In FIG. 13i) the temporary bridge restoration is viewed from the labial side such that part of the anatomical surface is seen.

In some cases the dentist prefers to have a physical combined model of a diagnostic wax-up and the patient's set of teeth. In that situation, the virtual combined model may be finalized by e.g. adding a base to it, and a physical combined model may then be manufactured based on the virtual combined model.

FIG. 14 illustrates the designing of at least a part of a dental component such as a temporary bridge restoration or a diagnostic wax-up bridge using an embodiment of the invention. The following description is made with reference to the case where the dental component is a temporary bridge restoration but the example is also valid for a diagnostic wax-up bridge.

Figure 14A:
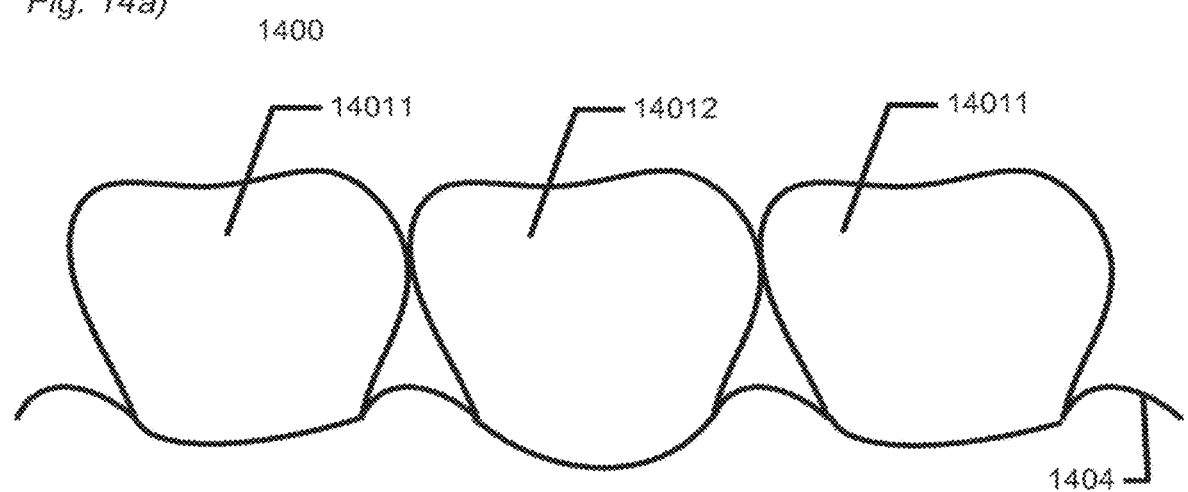
FIGS. 14a through 14f illustrate one workflow for designing of at least a part of a dental component such as a temporary bridge restoration or a diagnostic wax-up bridge using an embodiment of the invention.

FIG. 14a) shows an example of a 3D virtual model 1400 of a patient's teeth. The 3D virtual model 1400 may be obtained by 3D scanning the teeth with an intra-oral scanner, 3D scanning an impression of the teeth or 3D scanning a physical model of the teeth. The virtual model 1400 comprises three teeth 14011, 14012 where the middle one 14012 is to be extracted and replaced by a pontic, while the surrounding two teeth 14011 are to be prepared for accepting crown portions of the temporary bridge restoration.

The 3D scanning is performed before extracting the tooth 14012 from the patient's mouth and before the teeth 10411 are prepared. The teeth 10411 and 14012 may be virtually removed and virtual gingival and virtual preparations may be formed as described in FIG. 13.

Figure 14B:
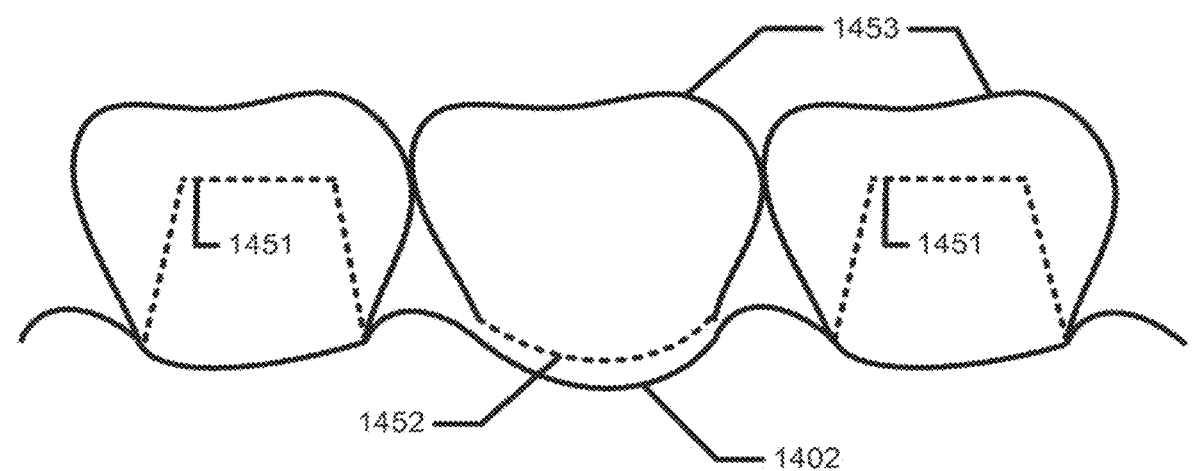

In FIG. 14b) an example of a jaw-facing surface 1451, 1452 of a temporary bridge restoration 1410 is illustrated. The jaw-facing surfaces 1451 of the crowns of the temporary bridge restoration are configured to allow the crowns to be attached to the corresponding teeth when these have been prepared by the dentist. The jaw-facing surfaces of the crowns may also be referred to as the cervical part of the crowns, i.e. the part facing the roots of the prepared teeth. The jaw-facing surface 1452 of the pontic may be generated by virtually removing the corresponding tooth from the 3D virtual model 1400 and forming a virtual gingival from which at least part of the jaw-facing surface 1452 is generated e.g. by offsetting the surface defined by the virtual gingival. The jaw-facing surface of the pontic may also be referred to as the basal part of the pontic.

The anatomical surface 1453 of the temporary bridge restoration may be generated from the original shape of the teeth 14011, 14012 or selected from a library of e.g. diagnostic wax-up templates.

Notice that the gap between the jaw-facing surface of the pontic 1453 and the adjacent edge of the gingival 1402 shown in this figure is exaggerated for the purpose of illustration. Still the gap should have a size so that the pontic does not irritate the adjacent gingival edge 1402.

Figure 14C:
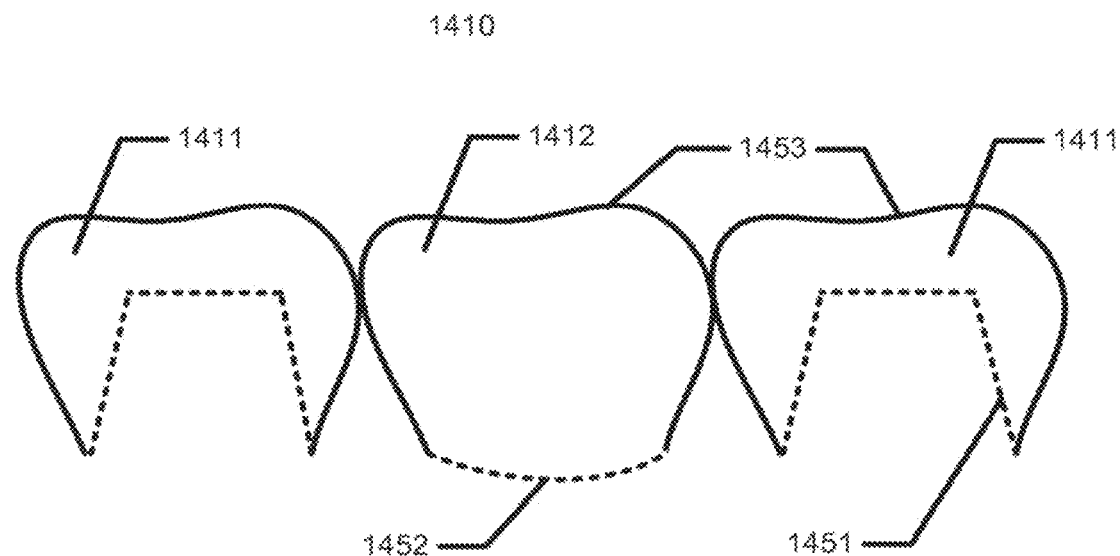

FIG. 14c) shows an example of the designed temporary bridge restoration 1410 with the pontic 1412 arranged between the two crowns 1411. The temporary bridge restoration may be manufactured prior to the preparation of the teeth such that it is available to be inserted into the patient's mouth immediately after the extraction and preparation of the teeth. When inserted in the mouth the jaw-facing surface of the crown portions will engage the prepared teeth while the jaw-facing surface of the pontic will face the gingival in the region where the tooth has been extracted. The temporary bridge restoration may be manufactured by e.g. direct digital manufacturing.

Figure 14D:
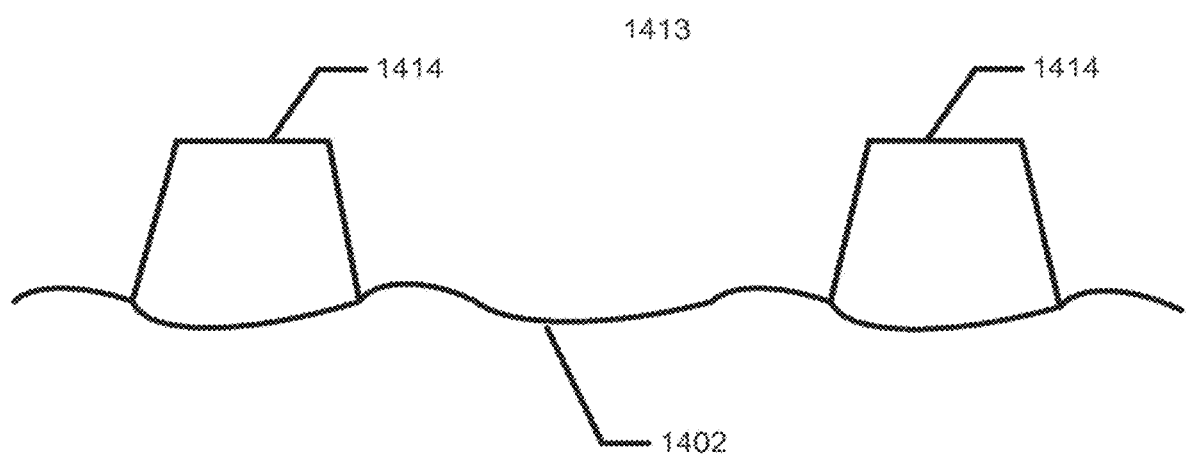

FIG. 14d) shows an example of the region 1413 of the teeth after the dentist has prepared the two teeth 14011 for the crowns and after the tooth 14012 has been extracted.

When the tooth has been extracted the surface in that region is shaped by the gingival 1402. The teeth 14011 from FIG. 14a) may have been prepared according to a virtual or physical dental preparation guide configured for providing the dentist guidance on how to ensure that the prepared teeth 1414 have a shape according to the jaw-facing surfaces 1451 of the temporary bridge restoration 1410 in FIG. 14c).

Figure 14E:
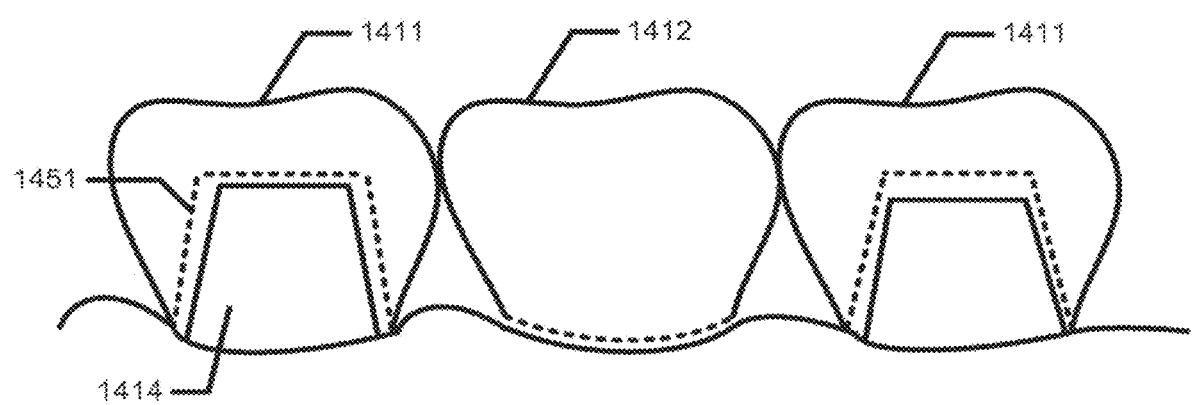

FIG. 14e) shows how the manufactured temporary bridge restoration may be fitted to the prepared teeth.

The preparation of the teeth is rarely such that the surface of the prepared teeth 1414 perfectly follows the jaw-facing surface 1451 of the crown portions of the temporary bridge restoration manufactured from the 3D virtual model of the same, but the preparation uncertainty and limitations of the manufacturing precision may be taken into account when designing the 3D virtual model such that the manufactured temporary bridge restoration still can be arranged at the prepared teeth. One way of doing so is by designing the crown parts using the so-called egg-shell design which ensures that the requirements to the precision of the shape of the prepared teeth are reduced.

Figure 14F:
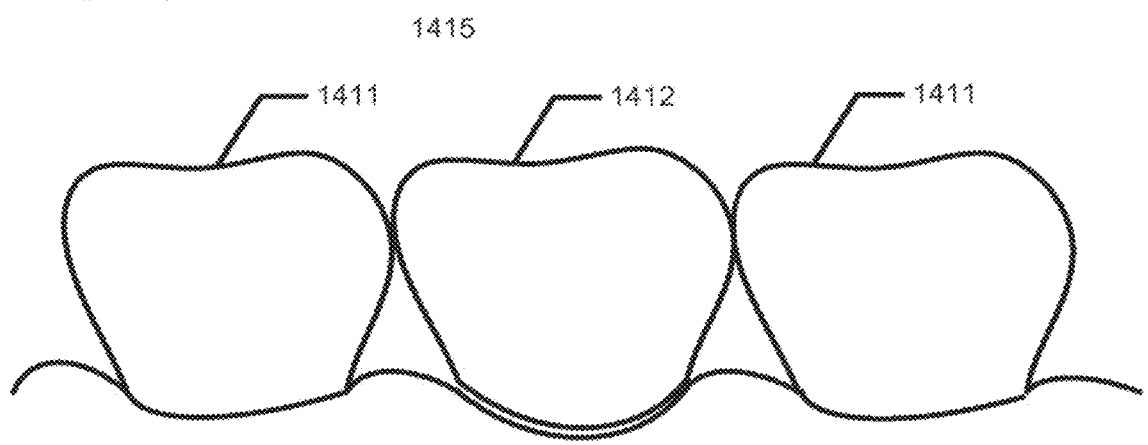

FIG. 14f) shows an example of the oral situation 1415 with the manufactured temporary bridge restoration arranged in the mouth of the patient. The temporary bridge restoration comprises a pontic 1412 and two crowns 1411, where the jaw-facing surface of the crowns and the surface of the prepared teeth are configured such that the temporary bridge restoration can be temporarily attached to the prepared teeth 1414.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention will now be described in more detail by means of the following sequentially numbered items.

1. A method for generating a 3D virtual model of a dental component for a region of a patient's set of teeth, where the dental component comprises a temporary bridge restoration or a diagnostic wax-up bridge, such that the dental component comprises crowns and at least one pontic, wherein the method comprises:
   obtaining a digital 3D representation of the set of teeth, where the digital 3D representation is based on a 3D scan of a pre-prepared configuration of the set of teeth;
   virtually sectioning the part of the digital 3D representation corresponding to the teeth in said region using at least one 3D sectioning spline;
   determining at least part of the inter-proximal surfaces of the virtually sectioned teeth; and
   determining a jaw-facing surface for the dental component, where the jaw-facing surface is configured for facing a surface which is not available in the digital 3D representation of the pre-prepared set of teeth.

2. The method according to item 1, wherein the jaw-facing surface comprises the jaw-facing surface of the pontic of said dental component.

3. The method according to item 1 or 2, wherein the jaw-facing surface comprises the jaw-facing surface of a least one of the crowns of said dental component.

4. The method according to any one or more of the preceding items, wherein determining the jaw-facing surface comprises estimating at least a part of the surface which is not available in the 3D representation.

5. The method according to any one or more of the preceding items, where the 3D sectioning spline for a tooth is adapted to extend over at least one inter-proximal surface of that tooth.

6. The method according to any one or more of the preceding items, wherein the 3D sectioning spline is defined automatically using a computer implemented sectioning spline generating algorithm.

7. The method according to any one or more of the preceding items, wherein the method comprises manually defining the 3D sectioning spline or manually adjusting an automatically generated 3D sectioning spline.

8. The method according to any one or more of the preceding items, wherein manually defining the 3D sectioning spline or manually adjusting an automatically generated 3D sectioning spline is based on sectioning spline control points used to control the shape of the 3D sectioning spline.

9. The method according to any one or more of the preceding items, wherein the method comprises virtually removing one or more teeth from the digital 3D representation, such as a tooth which is to be replaced by the pontic or a tooth which is to be prepared for accepting a crown.

10. The method according to any one or more of the preceding items, wherein the method comprises generating a virtual preparation for the tooth or a virtual gingival.

11. The method according to any one or more of the preceding items, wherein the virtual gingival is generated at the position in the digital 3D representation corresponding to the position at which the pontic is to be arranged.

12. The method according to any one or more of the preceding items, wherein at least a part of the dental component is designed based on the virtual gingival.

13. The method according to any one or more of the preceding items, wherein the method comprises replacing the virtually removed tooth with the virtual preparation or the virtual gingival in the digital 3D representation of the set of teeth.

14. The method according to any one or more of the preceding items, wherein the basal surface of the pontic is shaped according to the virtual gingival at the position in the digital 3D representation corresponding to where the pontic is to be arranged.

15. The method according to any one or more of the preceding items, wherein the virtual gingival is generated based on the digital 3D representation.

16. The method according to any one or more of the preceding items, wherein the virtual gingival is selected from a library of gingival profile templates or where the virtual gingival is generated by freeform modeling using flexible sculpt tools.

17. The method according to any one or more of the preceding items, wherein the selected virtual gingival is modified to fit the patient's set of teeth.

18. The method according to any one or more of the preceding items, wherein the method comprises generating a virtual margin line for a virtual preparation of at least one tooth in the digital 3D representation.

19. The method according to any one or more of the preceding claims, wherein the method comprises providing a diagnostic wax-up for the teeth of the dental component.

20. The method according to any of the previous items, wherein the method comprises generating a 3D virtual combined model by virtually replacing one or more teeth of the digital 3D representation with teeth according to the virtual diagnostic wax-up.

21. The method according to any of the previous items, wherein the method comprises hole-closure of the combined model such that holes appearing at the location where the diagnostic wax-up and the digital 3D representation connect are closed.

22. The method according to any of the previous items, wherein the method further comprises manufacturing a physical combined model from the 3D virtual combined model by direct digital manufacturing, such as by 3D printing or milling.

23. The method according to any one or more of the preceding items, wherein the method comprises projecting the virtual margin line onto the portion of the virtual diagnostic wax-up corresponding to that tooth.

24. The method according to any one or more of the preceding items, wherein the virtual margin line for a tooth is based on the 3D sectioning spline used for sectioning that tooth.

25. The method according to any one or more of the preceding items, wherein the virtual margin line for a tooth is substantially identical to the 3D sectioning spline for that tooth.

26. The method according to any one or more of the preceding items, wherein the boundary of the cervical surface of a crown part of the dental component is derived from said virtual margin line of the corresponding tooth.

27. The method according to any one or more of the preceding items, wherein the virtual margin line for a tooth is configured to extend over the inter-proximal surface of said tooth.

28. The method according to any one or more of the preceding items, wherein the virtual margin line is defined from the intersection of the virtual diagnostic wax-up and the digital 3D representation of the set of teeth in the combined model.

29. The method according to any one or more of the preceding items, wherein the virtual margin line is manually defined or wherein a section of an automatically generated virtual margin line is manually adjusted.

30. The method according to any one or more of the preceding items, wherein at least one anatomical surface of the 3D virtual model of the dental component is derived from the shape of the teeth in the pre-prepared configuration or from the virtual diagnostic wax-up.

31. The method according to any one or more of the preceding items, wherein the method comprises visualizing at least one virtual preparation using a visual display unit.

32. The method according to any one or more of the preceding items, wherein a part of the dental component is designed based on the virtual preparation.

33. The method according to any one or more of the preceding items, wherein the method comprises trimming the digital 3D representation of the set of teeth.

34. The method according to any one or more of the preceding items, wherein the inter-proximal surfaces are generated using polynomial algorithms to provide a realistic presentation of these surfaces.

35. The method according to any one or more of the preceding items, wherein the method comprises determining a target insertion direction for the dental component.

36. The method according to any one or more of the preceding items, wherein the 3D virtual model of the dental component is generated taking into account the target insertion direction for the dental component.

37. The method according to any one or more of the preceding items, wherein the crown parts of the dental component are shaped according to an egg-shell configuration 38. The method according to any one or more of the preceding items, wherein the virtual preparation is shaped according to the insertion direction.

39. The method according to any one or more of the preceding items, wherein the method is computer-implemented.

40. The method according to any of the previous items, wherein the method comprises modifying the digital 3D representation of the set of teeth by virtually replacing one or more teeth of the digital 3D representation with virtual preparations, and generating the 3D virtual model of the temporary bridge restoration with the crown parts corresponding to the prepared teeth.

41. The method according to any of the previous items, wherein the method further comprises manufacturing a physical model from the modified digital 3D representation of the set of teeth and/or the 3D virtual model of the temporary bridge restoration by direct digital manufacturing, such as by 3D printing or milling.

42. A method for manufacturing a dental component or a physical model of the dental component, where the method comprises:
    generating a 3D virtual model of the dental component using the method according to any of items 1 to 40; and
    manufacturing the dental component or the physical model of the dental component based on the 3D virtual model by direct digital manufacturing, such as by 3D printing or milling.

43. A method for manufacturing a combined model for use in planning, visualization and manufacturing of a bridge restoration, where the method comprises:
    obtaining a digital 3D representation of a pre-prepared set of teeth showing the region for which the bridge restoration is intended;
    providing a virtual diagnostic wax-up for the teeth of the bridge restoration;
    generating a 3D virtual combined model by virtually replacing one or more teeth of the digital 3D representation of the pre-prepared set of teeth with corresponding teeth of the virtual diagnostic wax-up; and manufacturing the combined model from the 3D virtual combined model by direct digital manufacturing, such as by 3D printing or milling.

44. A system for manufacturing a dental component, where the dental component comprises a temporary bridge restoration or a diagnostic wax-up bridge for a region of a patient's set of teeth such that the dental component comprises crowns and at least one pontic, said system comprising a non-transitory computer readable medium having one or more computer instructions stored thereon, where said computer instructions comprises instructions for generating a 3D virtual model of the dental component, where said generating comprises virtually sectioning the part of an obtained digital 3D representation corresponding to the teeth in said region using at least one 3D sectioning spline, determining at least part of the inter-proximal surfaces of the virtually sectioned teeth, and determining a jaw-facing surface for the dental component, where the jaw-facing surface is configured for facing a surface which is not available in the 3D representation; and a manufacturing device configured for manufacturing the dental component from said 3D virtual model.

45. The system according to item 43, wherein the system comprises a scanner device configured for obtaining a digital 3D representation of a set of teeth, such as an intra-oral scanner.

46. A method of designing a dental component for at least a region of a patient's set of teeth, wherein the method comprises:

obtaining a digital 3D representation of at least the region of the patient's set of teeth, where the digital 3D representation is based on a 3D scan, and where the teeth and gingival in the 3D representation are configured to be distinguished from each other;

virtually designing the dental component;

where at least part of the dental component is designed based on at least a part of the gingival in the 3D representation; and obtaining a 3D virtual model of the dental component.

47. The method according to any one or more of the preceding items, wherein the dental component is a restoration, a temporary restoration or a diagnostic wax-up.

48. The method according to any one or more of the preceding items, wherein the part of the dental component designed based on at least part of the gingival is a crown, a coping, a pontic, and/or a bridge.

49. The method according to any one or more of the preceding items, wherein the method comprises designing the edge of the dental component adjacent to the gingival part.

50. The method according to any one or more of the preceding items, wherein the method comprises designing a virtual gingival based on the gingival in the 3D representation, whereby the dental component is designed based on the virtual gingival.

51. The method according to any one or more of the preceding items, wherein the method comprises designing the virtual gingival by using one or more planes or curves.

52. The method according to any one or more of the preceding items, wherein the method comprises designing the virtual gingival to be convex or concave in shape.

53. The method according to any one or more of the preceding items, wherein the method comprises designing the virtual gingival by means of a gingival template.

54. The method according to any one or more of the preceding items, wherein the gingival template comprises at least three points configured for sculpting the gingival.

55. The method according to any one or more of the preceding items, wherein the method comprises virtually removing a tooth from the 3D representation, where the tooth is positioned in the place where a pontic of the dental component is configured to be arranged.

56. The method according to any one or more of the preceding items, wherein the method comprises virtually removing the tooth before designing the virtual gingival.

57. The method according to any one or more of the preceding items, wherein the method comprises virtually arranging a pontic in the place of a tooth.

58. The method according to any one or more of the preceding items, wherein the method comprises defining a gap between the edge of the pontic and the adjacent gingival.

59. A method of designing a dental component for a region on a patient's set of teeth, wherein the method comprises the steps of:

obtaining a digital 3D representation of at least the region of the patient's set of teeth, where the digital 3D representation is based on a 3D scan;

determining at least part of a surface which is not available in the 3D representation;

virtually designing a preparation in the region of the patient' set of teeth for the dental component; and obtaining a 3D virtual model of the dental component.

60. The method according to any one or more of the preceding items, wherein determining at least part of a surface not available in the 3D representation comprises virtually designing at least a part of the dental component.

61. The method according to any one or more of the preceding items, wherein the surface which is not available in the 3D representation is at least a part of the dental component being designed.

62. The method according to any one or more of the preceding items, wherein the surface which is not available in the 3D representation is an existing part of patient's set of teeth.

63. The method according to any one or more of the preceding items, wherein determining at least part of a surface which is not available in the 3D representation comprises determining a proximal side of a tooth.

64. The method according to any one or more of the preceding items, wherein determining at least part of a surface which is not available in the 3D representation comprises determining a sub-gingival tooth part.

65. The method according to any one or more of the preceding items, wherein determining at least part of a surface which is not available in the 3D representation is based on the 3D representation.

66. The method according to any one or more of the preceding items, wherein determining at least part of a surface which is not available in the 3D representation is based on the shape of neighbor teeth, and/or based on a default restoration.

67. The method according to any one or more of the preceding items, wherein determining at least part of a surface which is not available in the 3D representation is based on estimation by extrapolation of the 3D representation of the tooth.

68. The method according to any one or more of the preceding items, wherein the virtual design of at least part of dental component and/or of the preparation is based on at least part of the surface which is not available in the 3D representation.

69. The method according to any one or more of the preceding items, wherein the preparation is designed first, and at least part of the dental component is then designed based on the preparation.
70. The method according to any one or more of the preceding items, wherein the dental component is automatically derived when the preparation is designed.
71. The method according to any one or more of the preceding items, wherein at least part of the dental component is designed first, and the preparation is then designed based on the at least part of the dental component.
72. The method according to any one or more of the preceding items, wherein the preparation is automatically derived when at least part of the dental component is designed.
73. The method according to any one or more of the preceding items, wherein the preparation is designed or derived from the internal part of the dental component, such as the internal part of a crown. 74. The method according to any one or more of the preceding items, wherein the dental component is a restoration and/or a temporary restoration and/or a diagnostic wax-up.
75. The method according to any one or more of the preceding items, wherein the temporary restoration and/or restoration is a crown, a bridge, an implant and/or a veneer.
76. The method according to any one or more of the preceding items, wherein the crown comprises an internal part and an external part.
77. The method according to any one or more of the preceding items, wherein the shape of the internal part of the crown is equal to the shape of the preparation.
78. The method according to any one or more of the preceding items, wherein a cement space is defined between the internal part of the crown and the preparation.
79. The method according to any one or more of the preceding items, wherein the method further comprises designing structures in the inside surface of the crown.
80. The method according to any one or more of the preceding items, wherein the structures are shaped as grooves.
81. The method according to any one or more of the preceding items, wherein the method further comprises determining and visualizing a virtual margin line.
82. The method according to any one or more of the preceding items, wherein the method further comprises determining the virtual margin line from the 3D representation of the region of the patient's set of teeth.
83. The method according to any one or more of the preceding items, wherein the method further comprises arranging the virtual margin line to lie on the determined surface which was not available in the 3D representation.
84. The method according to any one or more of the preceding items, wherein the method further comprises connecting the virtual preparation with relevant available and/or estimated parts of a tooth in the region of the patient's set of teeth.
85. The method according to any one or more of the preceding items, wherein the method further comprises virtually snapping the preparation to the surface of the least one tooth in the region of the patient's set of teeth.
86. The method according to any one or more of the preceding items, wherein the preparation design is free-form designed, designed based on original tooth shape, designed based on the design of the dental component such as a crown, is a default design, is a parametric or algorithmic design, and/or is from a library.
87. The method according to any one or more of the preceding items, wherein the preparation design is based on which kind of tooth that is to be prepared, such as a molar tooth, a premolar tooth, or an anterior tooth.
88. The method according to any one or more of the preceding items, wherein the method further comprises designing the internal and/or external part of the crown based on the original tooth in the region of the patient's set of teeth.
89. The method according to any one or more of the preceding items, wherein the dental component is adapted to be attached in the region on the patient's set of teeth, after a physical preparation is performed on at least one tooth in the region on the patients' set of teeth.
90. The method according to any one or more of the preceding items, wherein the method further comprises determining a preparation guide for the dentist prior to preparing the teeth.
91. The method according to any one or more of the preceding items, wherein the method further comprises performing a virtual segmentation of at least part of the set of teeth.
92. The method according to any one or more of the preceding items, wherein the method further comprises virtually cutting out the at least one tooth in the region of the patient's set of teeth.
93. The method according to any one or more of the preceding items, wherein the method further comprises determining an insertion direction of the at least one tooth in the region of the patient's set of teeth.
94. The method according to any one or more of the preceding items, wherein the dental component is a temporary restoration, and the method further comprises designing a final restoration based on the design of the temporary restoration.
95. The method according to any one or more of the preceding items, wherein the method further comprises transferring the design of the temporary restoration into a design of a restoration by means of aligning the design of the temporary restoration with a 3D scan of the patient's prepared teeth.
96. The method according to any one or more of the preceding items, wherein the temporary design is modified prior to the transfer.
97. The method according to any one or more of the preceding items, where the temporary design is a one-layer design, and wherein the one-layer temporary design is converted to a two-layer restoration design.
98. The method according to any one or more of the preceding items, wherein the method further comprises performing validation scanning in the mouth of the patient with an intra-oral scanner while performing the preparation procedure according to the virtual design for validating that the preparation is performed correct according to the preparation guide.
99. The method according to any one or more of the preceding items, wherein the validation scanning provides a real time validation.
100. The method according to any one or more of the preceding items, wherein the 3D scan is an intra-oral scan of at least part of the patient's set of teeth, a scan of at least part of an impression of the patient's set of teeth, and/or a scan of at least part of a model of the patient's set of teeth.
101. The method according to any one or more of the preceding items, wherein the 3D scan is performed by means of laser light scanning, white light scanning, probe-scanning, X-ray scanning, and/or CT scanning.

102. A computer program product comprising program code means for causing a data processing system to perform the method of any one of the preceding items when said program code means are executed on the data processing system.

103. A computer program product according to the previous item, comprising a computer-readable medium having stored there on the program code means.

104. A non-transitory computer readable medium storing thereon a computer program, where said computer program is configured for causing computer-assisted data processing to perform the method of any one of items 1 to 100, when the program code means are executed on the data processing system 105. A system for designing a dental component for a region on a patient's set of teeth, wherein the system comprises:
 means for obtaining a digital 3D representation of at least the region of the patient's set of teeth, where the digital 3D representation is based on a 3D scan;
 means for determining at least part of a surface which is not available in the 3D representation;
 means for virtually designing a preparation in the region of the patient' set of teeth for the dental component; and
 means for obtaining a 3D virtual model of the dental component.

106. A system for designing a dental component for at least a region of a patient's set of teeth, wherein the system comprises:
 means for obtaining a digital 3D representation of at least the region of the patient's set of teeth, where the digital 3D representation is based on a 3D scan, and where the teeth and gingival in the 3D representation are configured to be distinguished from each other;
 means for virtually designing the dental component;
 where at least part of the dental component is designed based on at least a part of the gingival in the 3D representation; and
 means for obtaining a 3D virtual model of the dental component.

The invention claimed is:

1. A computer program product encoded on a non-transitory computer readable medium for generating a digital 3D combined model for use in planning and visualization of a dental component based on a digital 3D model of the dental component showing a desired shape of the teeth of the dental component and a digital 3D representation of a pre-prepared set of teeth showing the region for which the dental component is intended, said computer program product comprising computer-executable instructions for causing a data processing system to generate a digital 3D combined model representing a target dental situation for the patient when the dental component is arranged at the teeth, where the computer-executable instructions are configured for digitally replacing one or more teeth of the digital 3D representation of the pre-prepared set of teeth with the digital 3D model of the dental component by digitally removing the one or more teeth of the digital 3D representation of the pre-prepared set of teeth and digitally adding the digital 3D model of the dental component to the digital 3D representation of the pre-prepared set of teeth.

2. The computer program product according to claim 1, wherein a 3D sectioning spline is created in relation to the digital 3D representation of the pre-prepared set of teeth, and the portion of the digital 3D representation of the pre-prepared set of teeth which is deleted when removing at least one tooth is defined and bounded by said 3D sectioning spline.

3. The computer program product according to claim 1, wherein generating the digital 3D combined model comprises generating an inter-proximal surface configured for closing an inter-proximal part of a hole formed in the digital 3D representation of the pre-prepared set of teeth by the digital removal of a tooth.

4. The computer program product according to claim 3, wherein the inter-proximal surface is generated based on the shape of a neighboring tooth.

5. The computer program product according to claim 4, wherein the inter-proximal surface is generated using a polynomial algorithm.

6. The computer program product according to claim 1, wherein generating the digital 3D combined model comprises generating a digital gingiva configured for closing a gingival part of the hole in the digital 3D representation of the pre-prepared set of teeth resulting from the digital removal of a tooth.

7. The computer program product according to claim 6, wherein the digitally removed tooth at least partly is replaced with the generated digital gingiva.

8. The computer program product according to claim 6, wherein the digital gingiva is generated based on the digital 3D representation of the pre-prepared set of teeth.

9. The computer program product according to claim 8, wherein the digital gingiva is generated based on part of the digital 3D representation of the pre-prepared set of teeth expressing the shape of the surrounding gingiva.

10. The computer program product according to claim 8, wherein generating the digital gingiva comprises selecting a gingiva profile template from a library of gingiva profile templates and modifying the selected gingiva profile template to fit the patient's set of teeth.

11. The computer program product according to claim 6, wherein the digital gingiva at least partly is shaped using a number of control points assigned to the digital gingiva.

12. The computer program product according to claim 6, wherein the digital gingival is generated at the position in the digital 3D representation corresponding to the position at which a pontic of the dental component is to be arranged.

13. The computer program product according to claim 1, wherein the computer program product comprises instructions for hole-closure of the digital 3D combined model such that holes appearing at the location where the 3D digital model of the dental component and the digital 3D representation connect are closed.

14. The computer program product according to claim 1, wherein the dental component is a bridge restoration.

15. The computer program product according to claim 1, wherein the computer program product comprises instructions for controlling equipment for direct digital manufacturing of a physical combined model from the digital 3D combined model.

\* \* \* \* \*